(12) United States Patent
O'Harte et al.

(10) Patent No.: US 7,326,688 B2
(45) Date of Patent: *Feb. 5, 2008

(54) ANALOGS OF GASTRIC INHIBITORY POLYPEPTIDE AND THEIR USE OF TREATMENT FOR DIABETES

(75) Inventors: Finbarr Paul Mary O'Harte, Coleraine Co Londonderry (GB); Peter Raymond Flatt, Coleraine Co. Londonderry (GB)

(73) Assignee: UUTech Limited, Coleraine (GB)

( * ) Notice: Subject to any disclaimer, the term of this patent is extended or adjusted under 35 U.S.C. 154(b) by 95 days.

This patent is subject to a terminal disclaimer.

(21) Appl. No.: 11/090,825

(22) Filed: Mar. 25, 2005

(65) Prior Publication Data

US 2005/0277590 A1    Dec. 15, 2005

Related U.S. Application Data

(63) Continuation of application No. 09/937,687, filed as application No. PCT/GB00/01089 on Mar. 29, 2000, now Pat. No. 6,921,748.

(30) Foreign Application Priority Data

Mar. 29, 1999  (GB) ................... 9907216.7
Jul. 29, 1999   (GB) ................... 9917565.5

(51) Int. Cl.
*A61K 38/22*   (2006.01)
*C07K 14/575*  (2006.01)

(52) U.S. Cl. ................... 514/12; 514/13; 514/14; 514/21; 530/324; 530/325; 530/326

(58) Field of Classification Search ................ None
See application file for complete search history.

(56) References Cited

U.S. PATENT DOCUMENTS 5,998,204  A      12/1999  Tsien et al.
6,921,748  B1 *   7/2005   O'Harte et al. ............... 514/12

FOREIGN PATENT DOCUMENTS

DE    196 16 486 A1    10/1997
EP    0 869 135 A1     10/1998

OTHER PUBLICATIONS

Demuth, et al., *Chemical Abstracts* 127:69 abstract 341803D (1997).
Fujii et al., *Chem. Pharm. Bull.* 34(6):2397-2410 (1986) "Studies on Peptides. CXXXIX. Solution synthesis of a 42-residue peptide corresponding to the entire amino acid sequence of human glucose-dependent insulinotropic polypeptide (GIP)".

(Continued)

*Primary Examiner*—Jeffrey Edwin Russel
(74) *Attorney, Agent, or Firm*—Kirkpatrick & Lockhart Preston Gates Ellis LLP

(57) ABSTRACT

The present invention provides peptides which stimulate the release of insulin. The peptides, based on GIP 1-42 include substitutions and/or modifications which enhance and influence secretion and/or have enhanced resistance to degradation. The invention also provides a process of N terminally modifying GIP and the use of the peptide analogues for treatment of diabetes.

135 Claims, 32 Drawing Sheets

OTHER PUBLICATIONS

Gallwitz et al., *J. Mol. Endocrinology* 10:259-268 (1993) "Binding specificity and signal transduction of receptors for glucagon-like peptide-1(7-36)amide and gastric inhibitory polypeptide on RINm5F insulinoma cells".

Gallwitz et al., *Regulatory Peptides* 63:17-22 (1996) "GLP-1/GIP chimeric peptides define the structural requirements for specific ligand-receptor interaction of GLP-1".

Gault et al., *Digestion* 60:504-505 (1999) "Stability of GIP and Amino-Terminally Modified GIP Analogues to DPP IV and Human Plasma," Scientific Meeting of the Bayliss & Starling Society, Belfast, N. Ireland, Sep. 5-8, 1999.

Gelling et al., "Minor N-terminal modification of glucose-dependent insulinotropic polypeptide (GIP) greatly reduces receptor binding and insulinotropic activity: evidence that N-terminal residues are essential for biological activity," Abstract P2-29, Tenth International Congress of Endocrinology, Jun. 12-13, 1996, San Francisco, USA.

Gelling et al., *Endocrinology* 138:2640-2643 (1997) "Localization of the domains involved in ligand binding and activation of the glucose-dependent insulin tropic polypeptide receptor".

Gelling et al., *Regulatory Peptides* 69:151-154 (1997) "GIP$_{6-30amide}$ contains the high affinity binding region of GIP and is a potent inhibitor of GIP$_{1-42}$ action in vitro".

Gelling, Ph.D. Thesis, Oct. 1998, "Structure-function studies of the gastric inhibitory polypeptide/glucose dependent insulinotropic polypeptide (GIP) receptor".

Jornvall et al., *FEBS Letters* 123:205-210 (1981) "Amino acid sequence and heterogeneity of gastric inhibitory polypeptide (GIP)".

Kühn-Wache et al., "Analogs of glucose-dependent insulinotropic polypeptide with increased dipeptidyl peptidase IV resistance," in Cellular Peptidases in Immune Functions and Diseases 2, Proceedings of an international conference. Sep. 12-14, 1999, Magdeburg-Herrenkrug, Germany, ed. Langer & Ansorge, Kluwer Academic/Plenum Publishers, 2000.

Kurtzhals et al., *Biochem. J.* 312:725-731 (1995) "Albumin binding of insulins acylated with fatty acids: characterization of the ligand-protein interaction and correlation between binding affinity and timing of the insulin effect in vivo".

McIntosh et al., *Acta Physiol. Scand.* 157:361-365 (1996) "GIP receptors and signal-transduction mechanisms".

Mentlein, *FEBS Letters* 234:251-256 (1988) "Proline residues in the maturation and degradation of peptide hormones and neuropeptides".

Mentlein et al., *Eur. J. Biochem.* 214:829-835 (1993) "Dipeptidyl-peptidase IV hydrolyses gastric inhibitory polypeptide, glucagon-like peptide-1(7-36)amide, peptide histidine methionine and is responsible for their degradation in human serum".

Mooney et al., *Digestsion* 60:505 (1999) "Effect of Tyr$^1$-Glucitol GIP on Insulin Release and Glucose Homeostasis in Obese Diabetic Mice," Scientific Meeting of the Bayliss & Starling Society, Belfast, N. Ireland, Sep. 5-8, 1999.

O'Harte et al., *Biochim. Biophys. Acta.* 1425:319-327 (1998) "Amino terminal glycation of gastric inhibitory polypeptide enhances its insulinotropic action on clonal pancreatic B-cells".

O'Harte et al., *Chemical Abstracts* 131:122 (1999) "NH$_2$—terminally modified gastric inhibitory polypeptide exhibits aminopeptidase resistance and enhanced anti-hyperglycemic activity" (was cited in parent patent).

O'Harte et al., *Diabetes* 48:758-765 (1999) "NH$_2$-terminally modified gastric inhibitory polypeptide exhibits aminopeptidase resistance and enhanced anti-hyperglycemic activity".

O'Harte et al., *J. Endocrinology* 165:639-648 (2000) "Improved glycaemic control in obese diabetic ob/ob mice using N-terminally modified gastric inhibitory polypeptide."

Rossowski et al., *Regulatory Peptides* 39:9-17 (1992) "Reduced gastric acid inhibitory effect of a pGIP(1-30)NH$_2$ fragment with potent pancreatic amylase inhibitory activity".

Schmidt et al., *Endocrinology* 120:835-837 (1987) "Commercially available preparations of porcine glucose-dependent insulinotropic polypeptide (GIP) contain a biologically inactive GIP-fragment and cholecystokinin-33/-39".

* cited by examiner

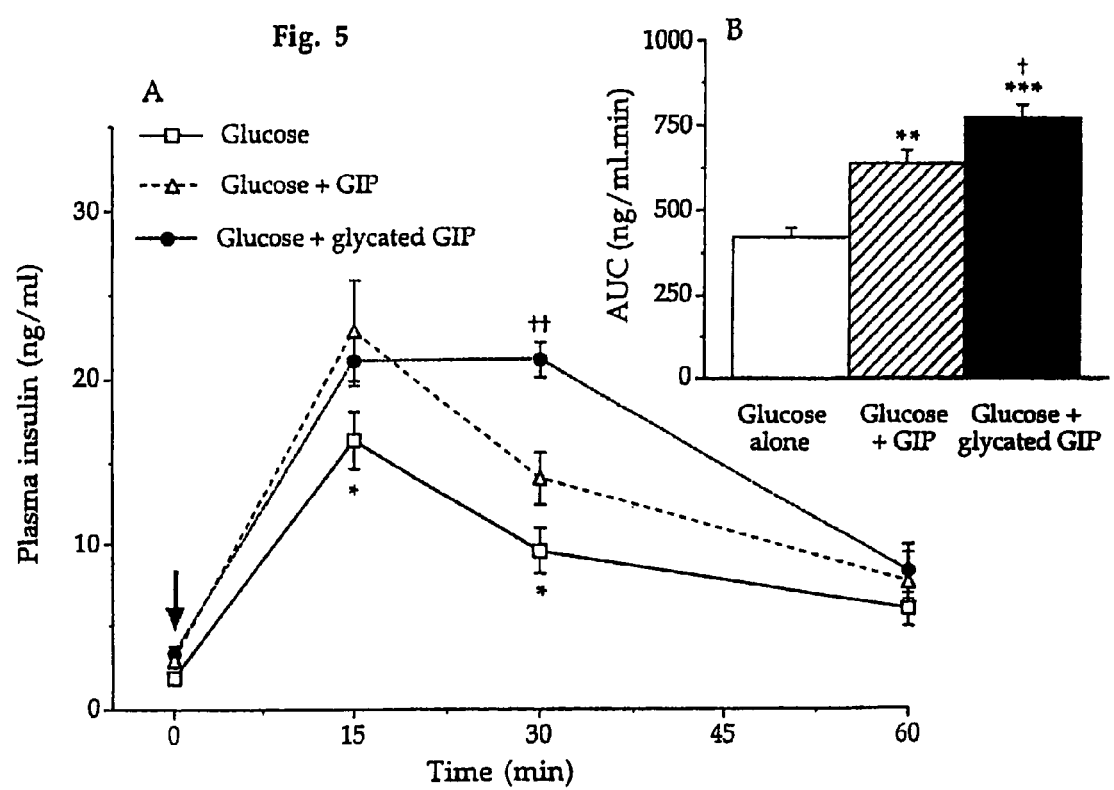

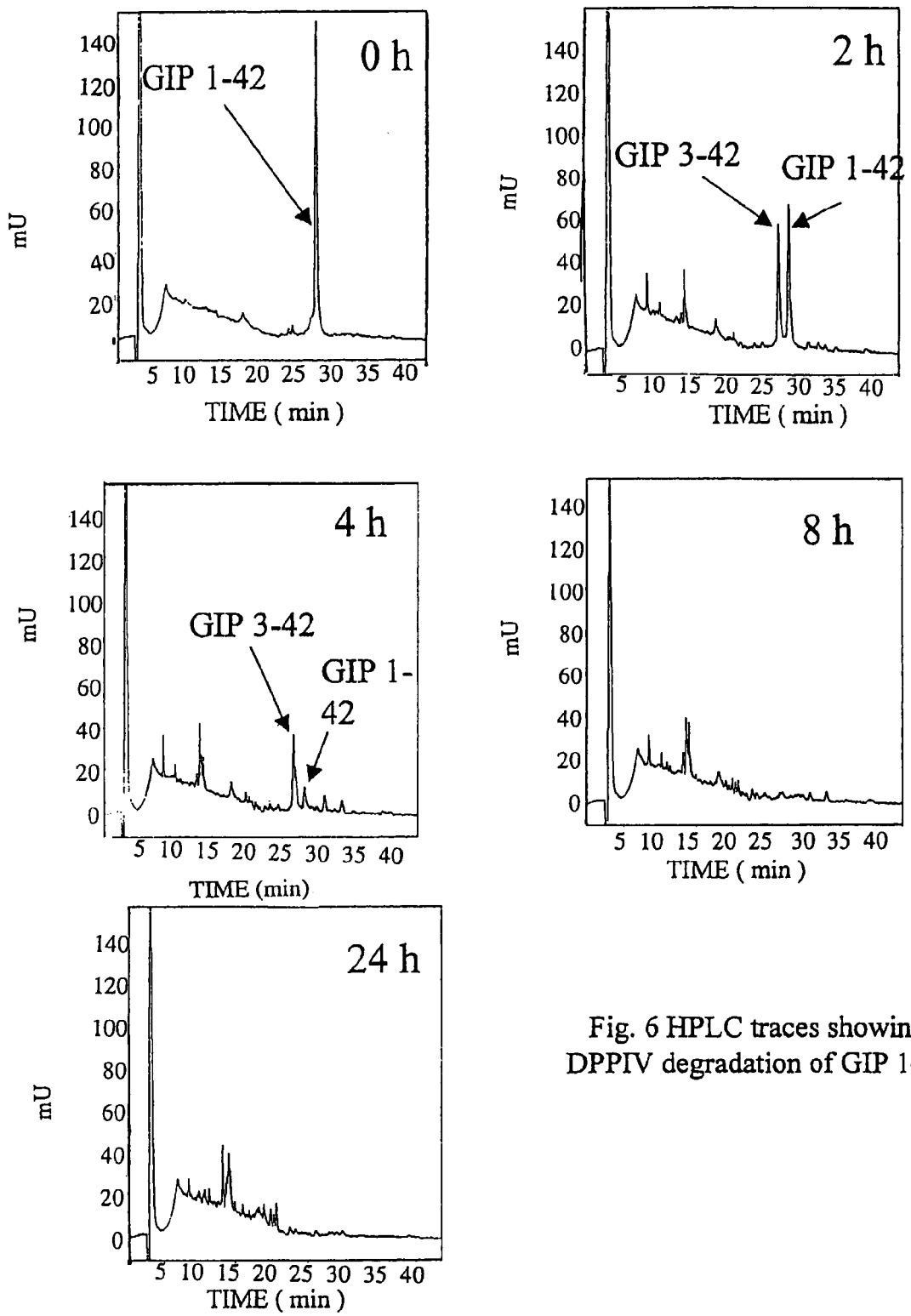
Fig. 6 HPLC traces showing DPPIV degradation of GIP 1-42

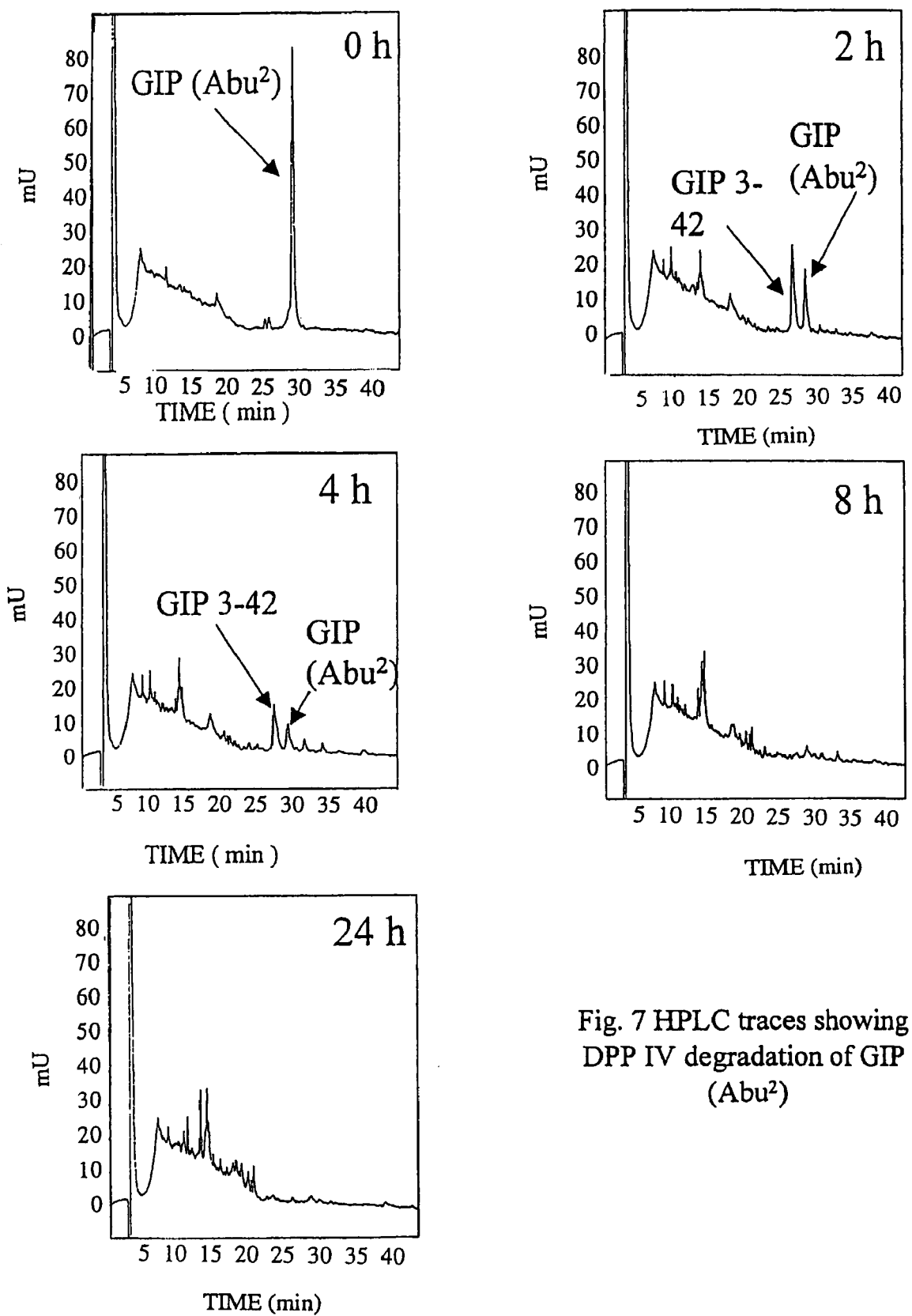
Fig. 7 HPLC traces showing DPP IV degradation of GIP (Abu²)

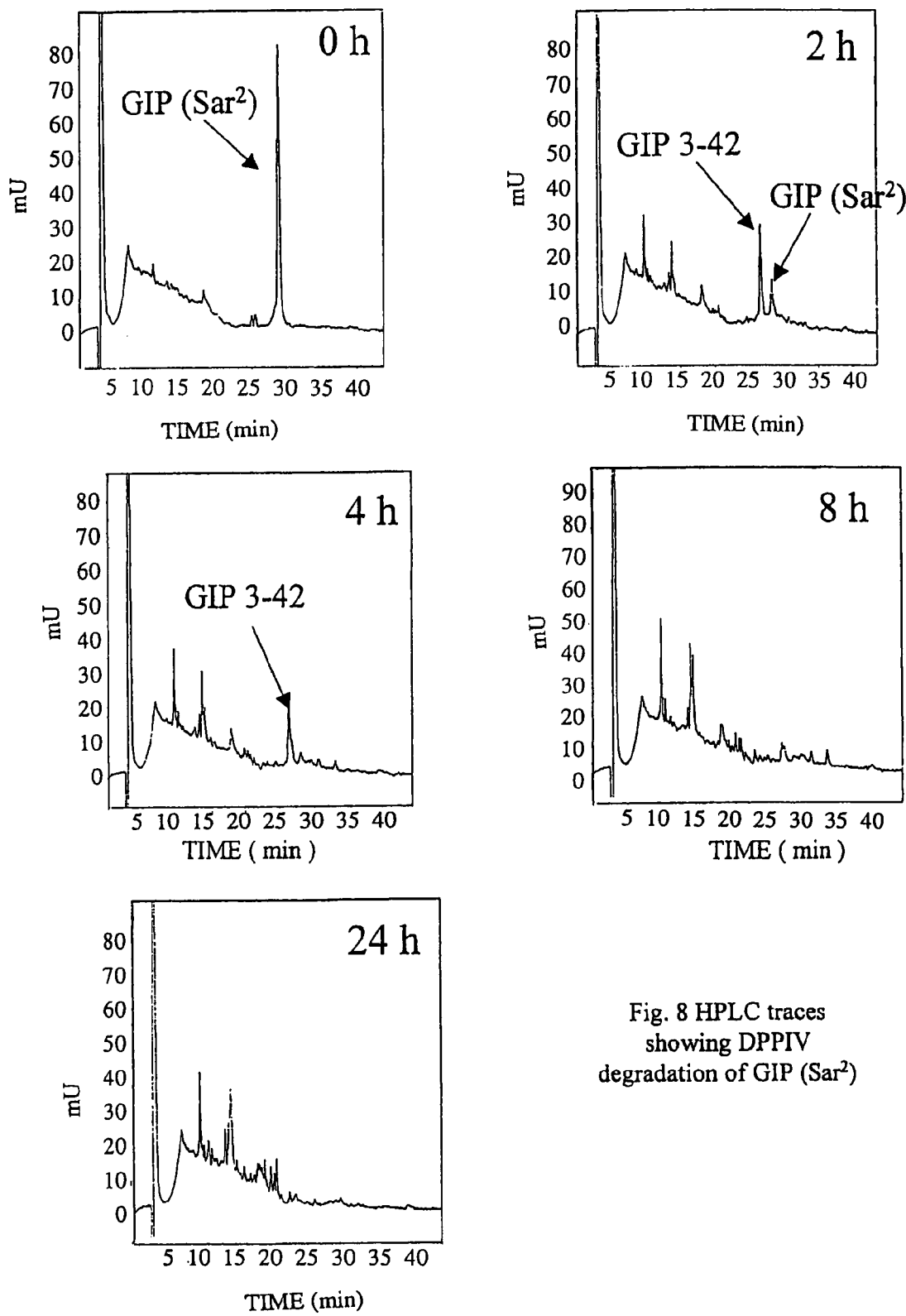
Fig. 8 HPLC traces showing DPPIV degradation of GIP (Sar$^2$)

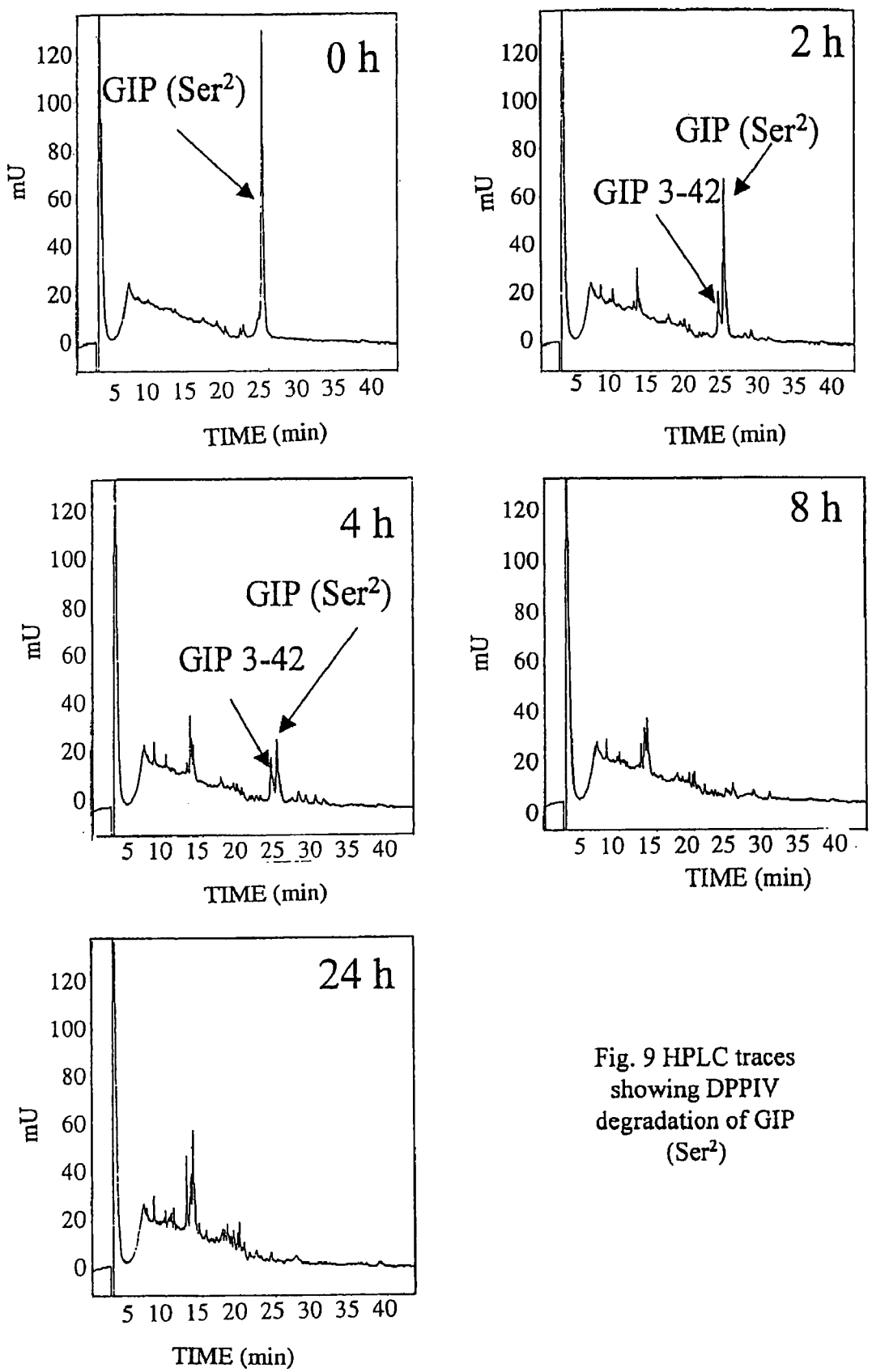
Fig. 9 HPLC traces showing DPPIV degradation of GIP (Ser$^2$)

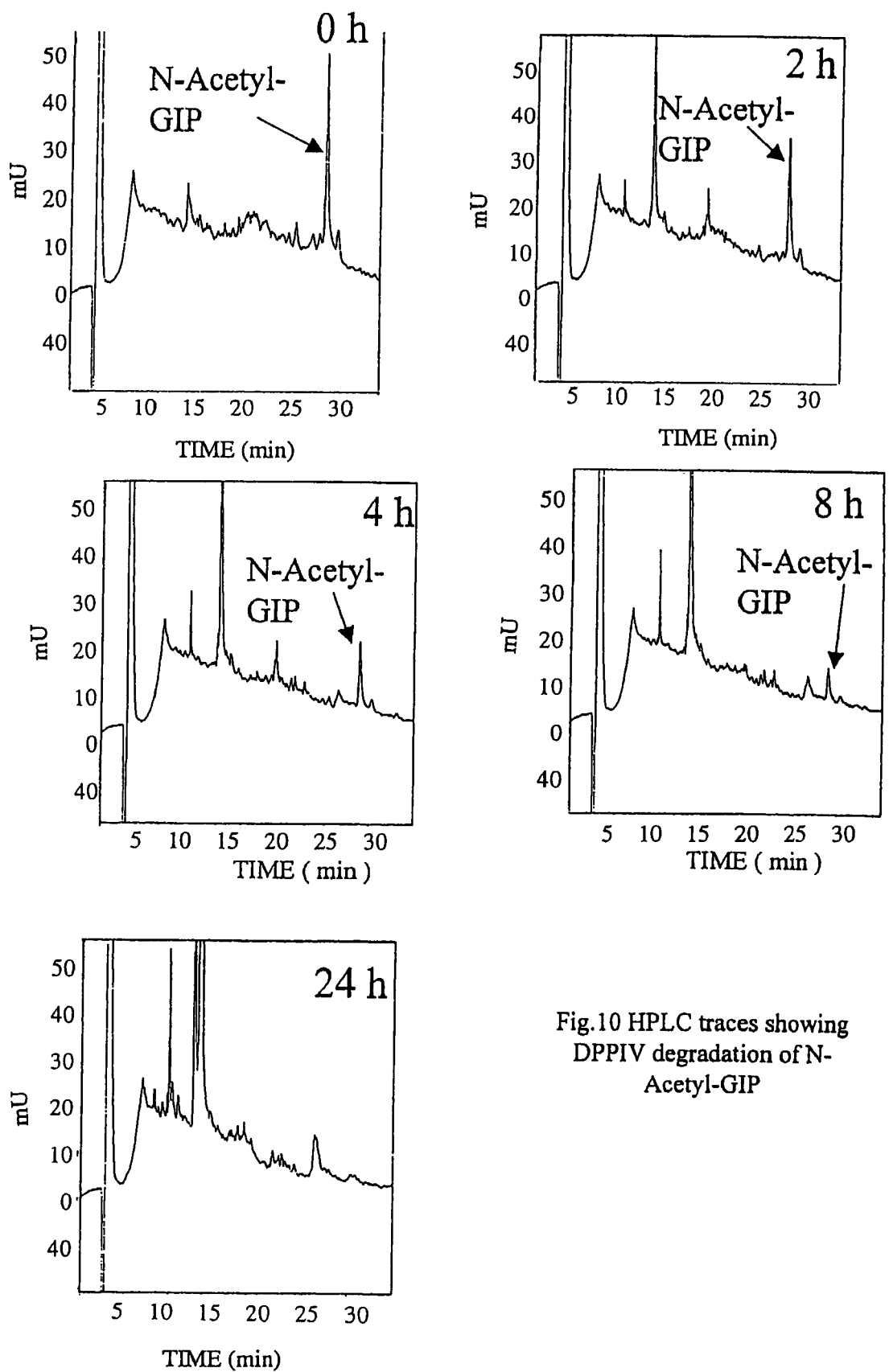
Fig.10 HPLC traces showing DPPIV degradation of N-Acetyl-GIP

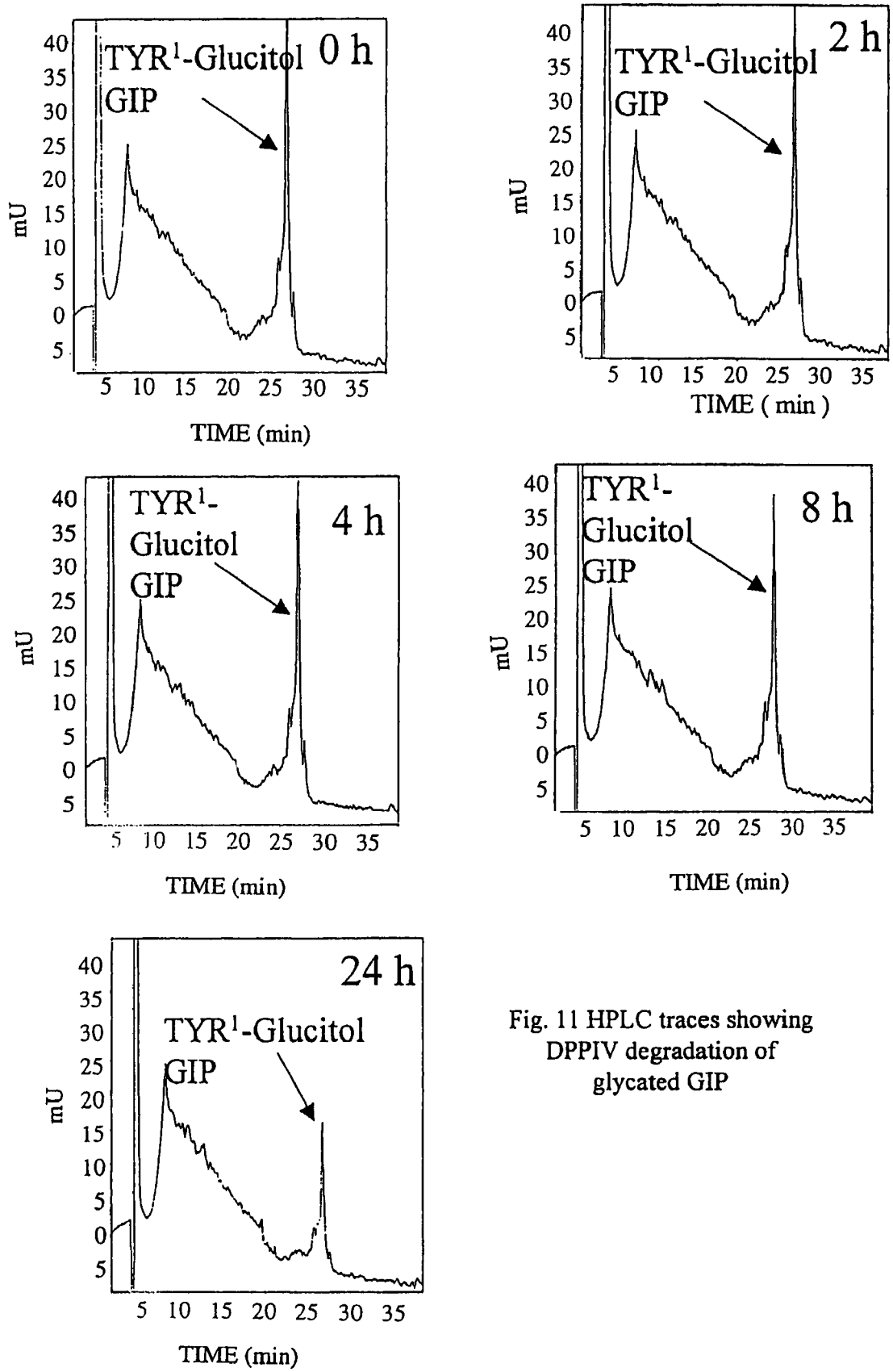
Fig. 11 HPLC traces showing DPPIV degradation of glycated GIP

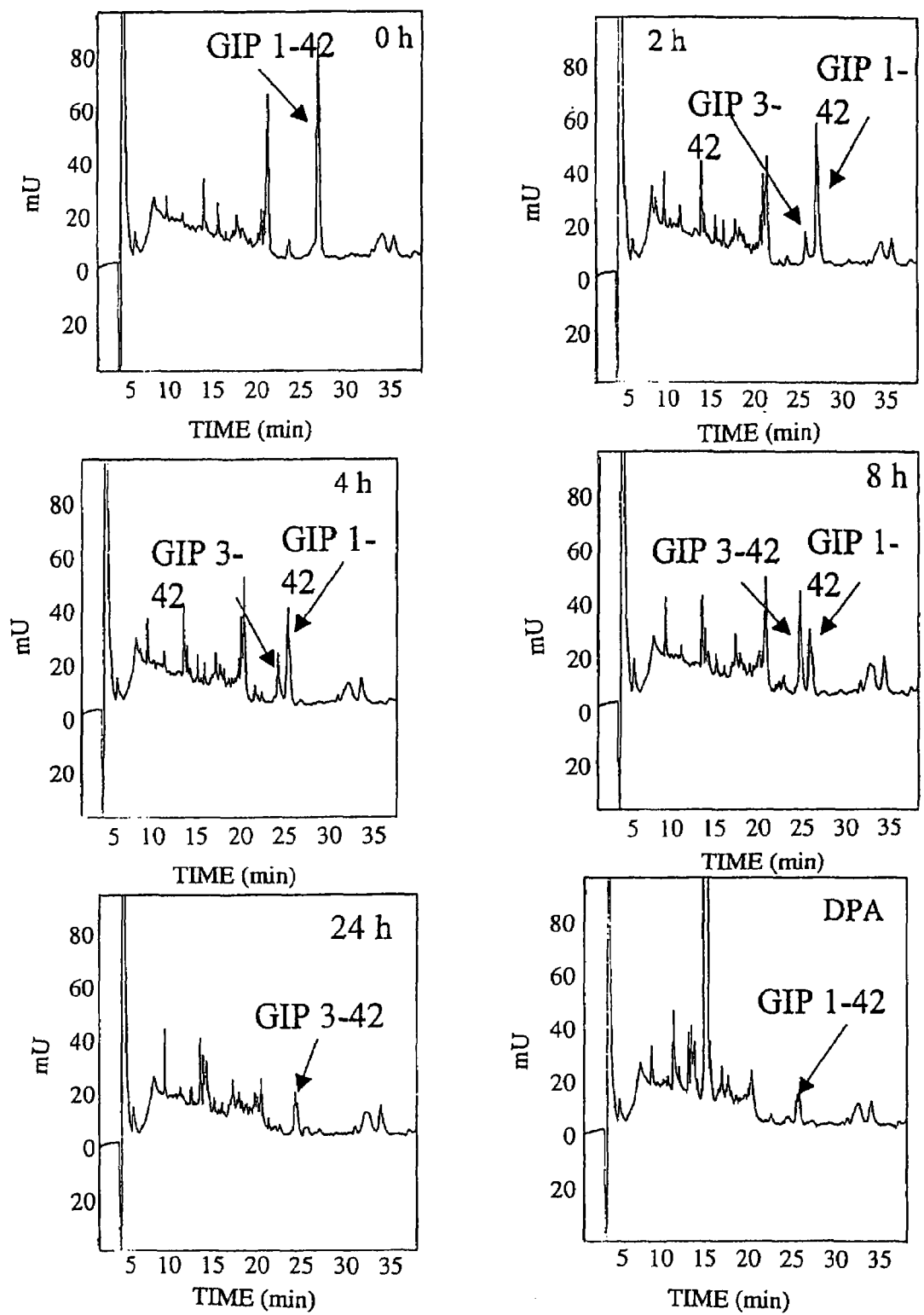
Fig.12. HPLC traces showing human plasma degradation of GIP

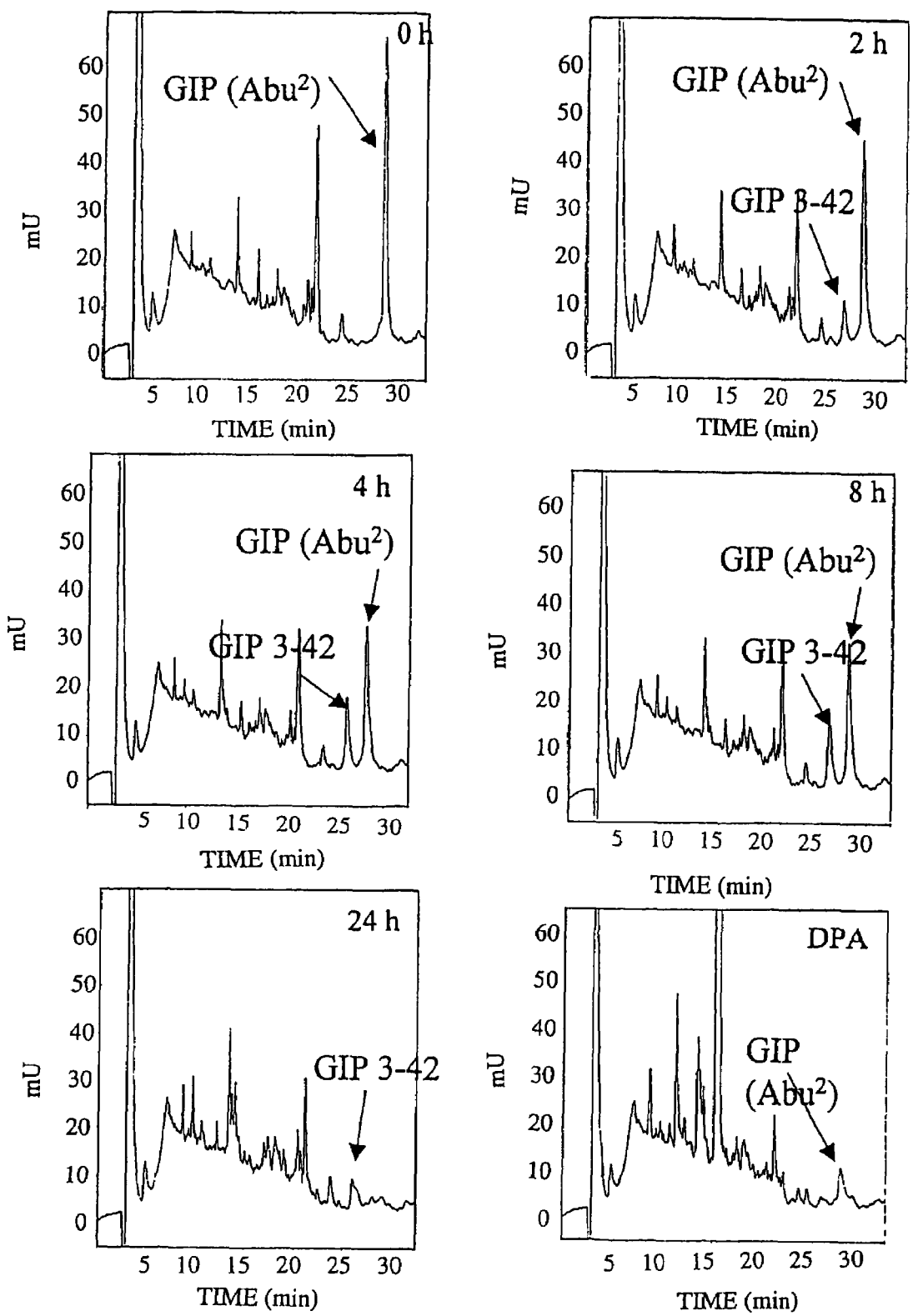
Fig. 13. HPLC traces showing human plasma degradation of GIP (Abu$^2$)

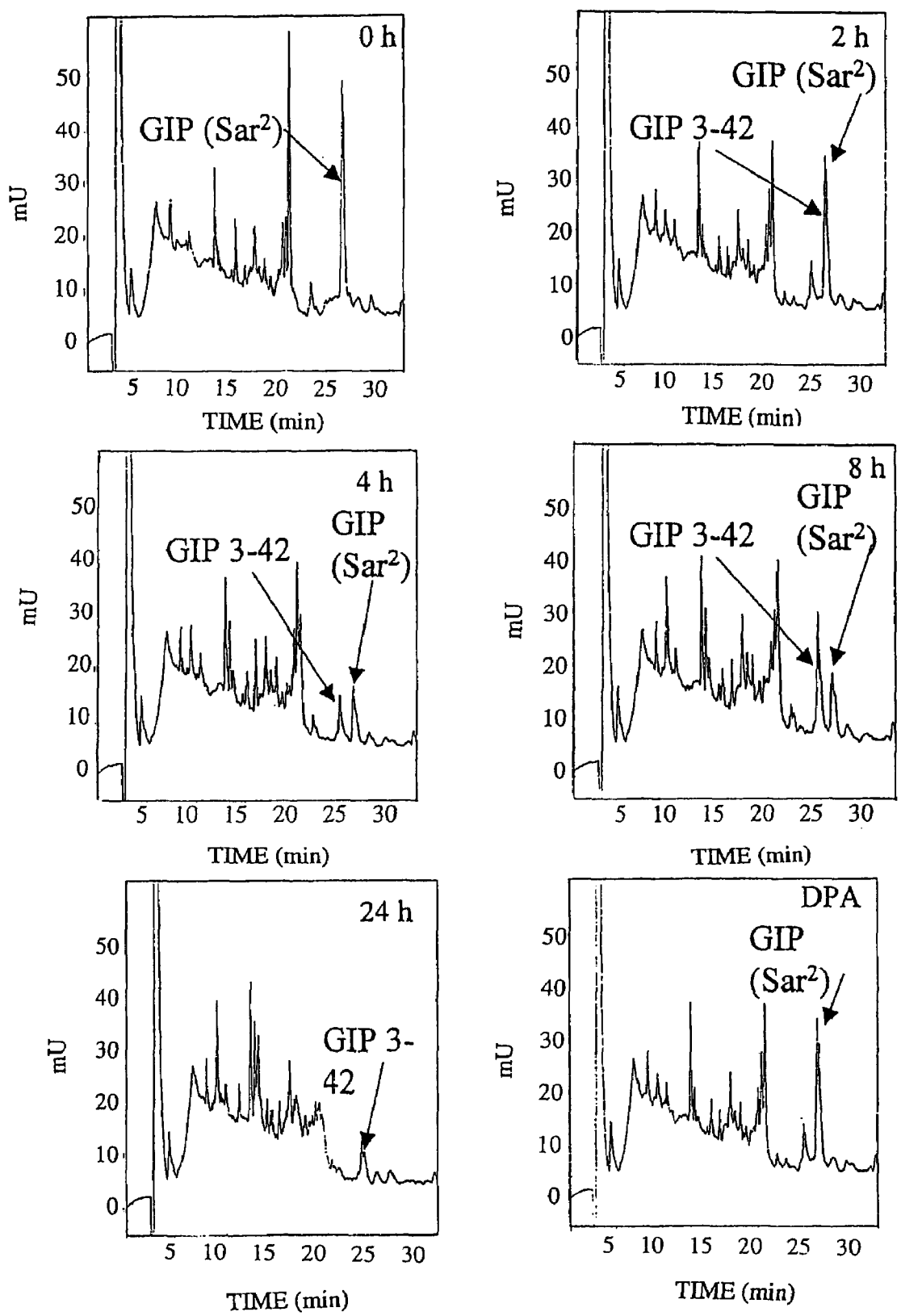
Fig. 14. HPLC traces showing human plasma degradation of GIP (Sar$^2$)

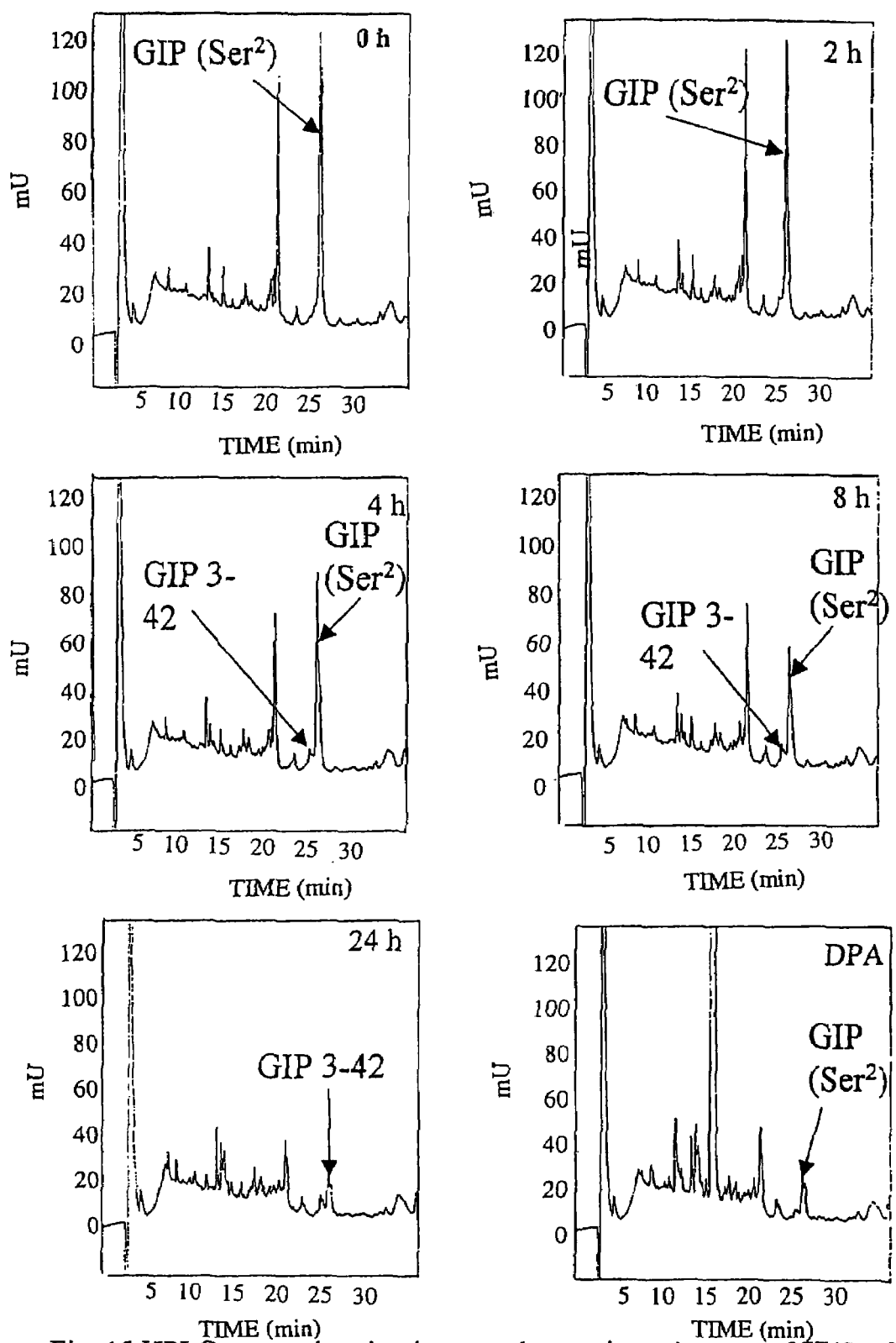
Fig. 15 HPLC traces showing human plasma degradation of GIP(Ser$^2$)

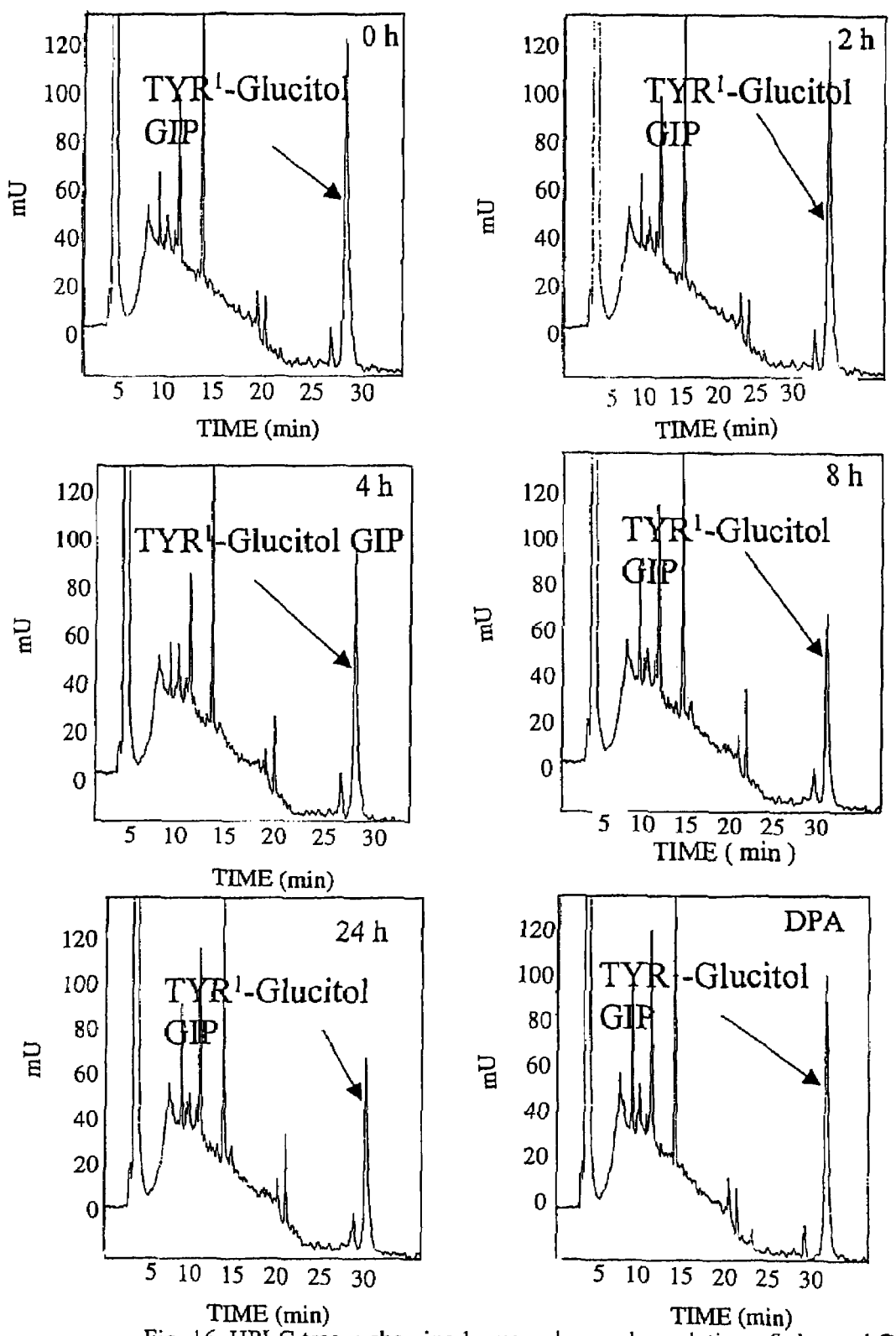
Fig. 16. HPLC traces showing human plasma degradation of glycated GIP.

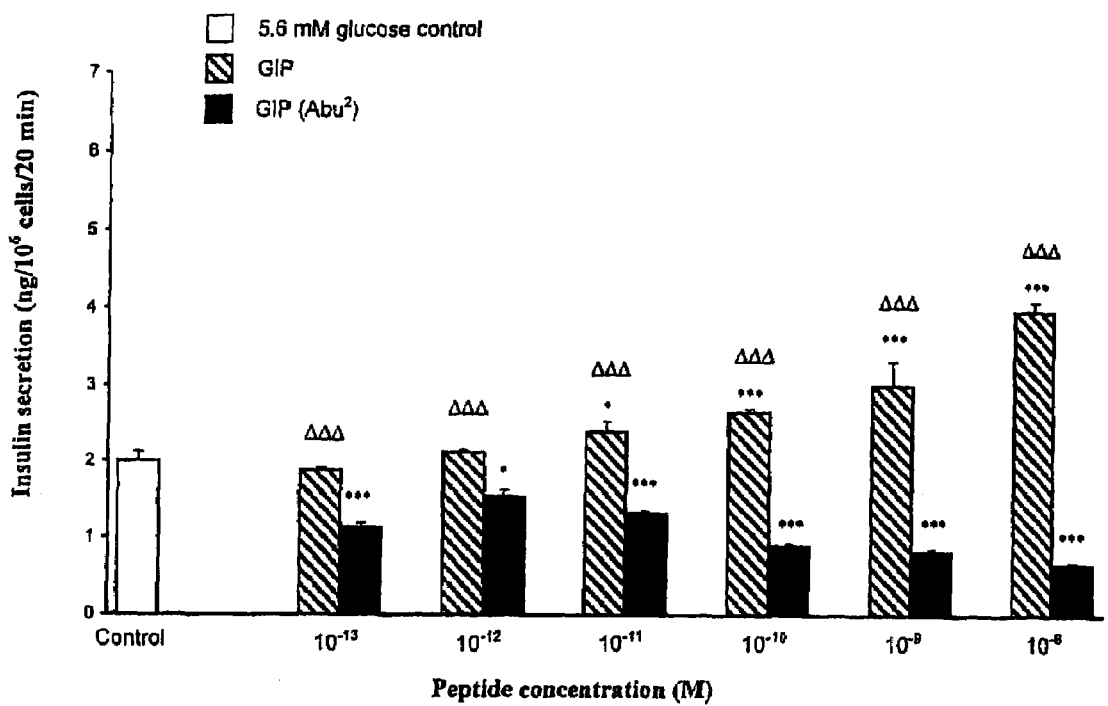
Fig.17. Graph showing the effects of various concentrations of GIP and GIP (Abu$^2$) on insulin release from BRIN-BD11 cells incubated at 5.6 mM glucose
Values are means ± S.E.M. for 12 separate observations. $^*P< 0.05$, $^{}P< 0.01$, $^{*}P<0.001$ compared to control (5.6mM glucose alone). $^{\Delta}P<0.05$, $^{\Delta\Delta}P<0.01$, $^{\Delta\Delta\Delta}P<0.001$ compared to GIP (Abu$^2$) at the same concentration.

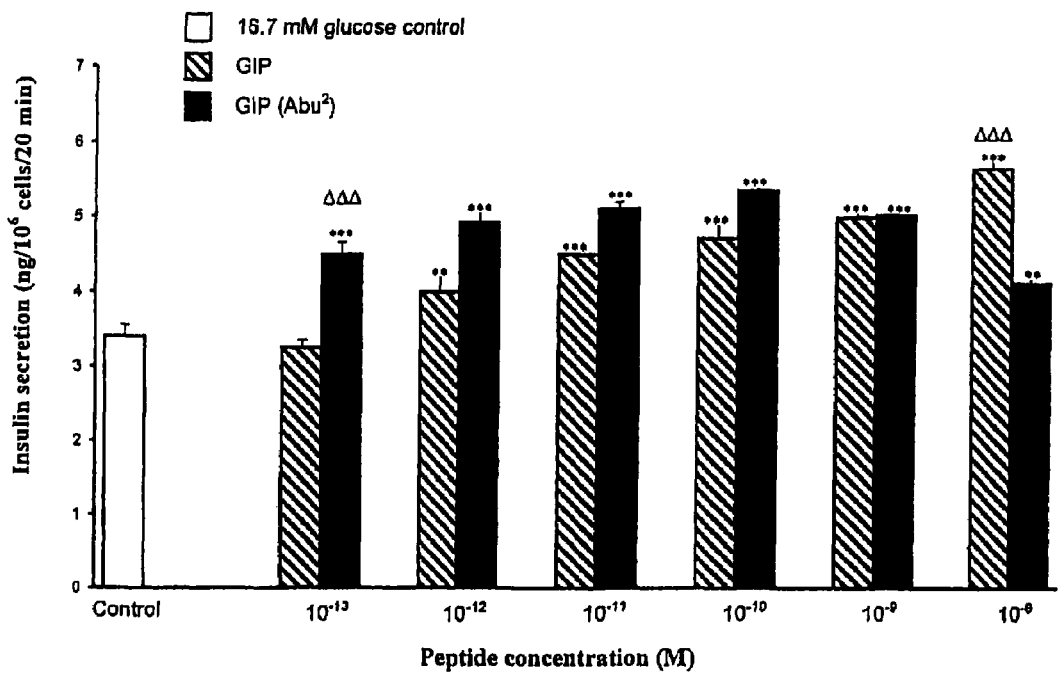
Fig. 18. Graph showing the effects of various concentrations of GIP and GIP (Abu$^2$) on insulin release from BRIN-BD11 cells incubated at 16.7 mM glucose
Values are means ± S.E.M. for 12 separate observations. $^*P< 0.05$, $^{}P< 0.01$, $^{*}P<0.001$ compared to control (16.7 mM glucose alone). $^{\Delta}P<0.05$, $^{\Delta\Delta}P<0.01$, $^{\Delta\Delta\Delta}P<0.001$ compared to GIP (Abu$^2$) at the same concentration.

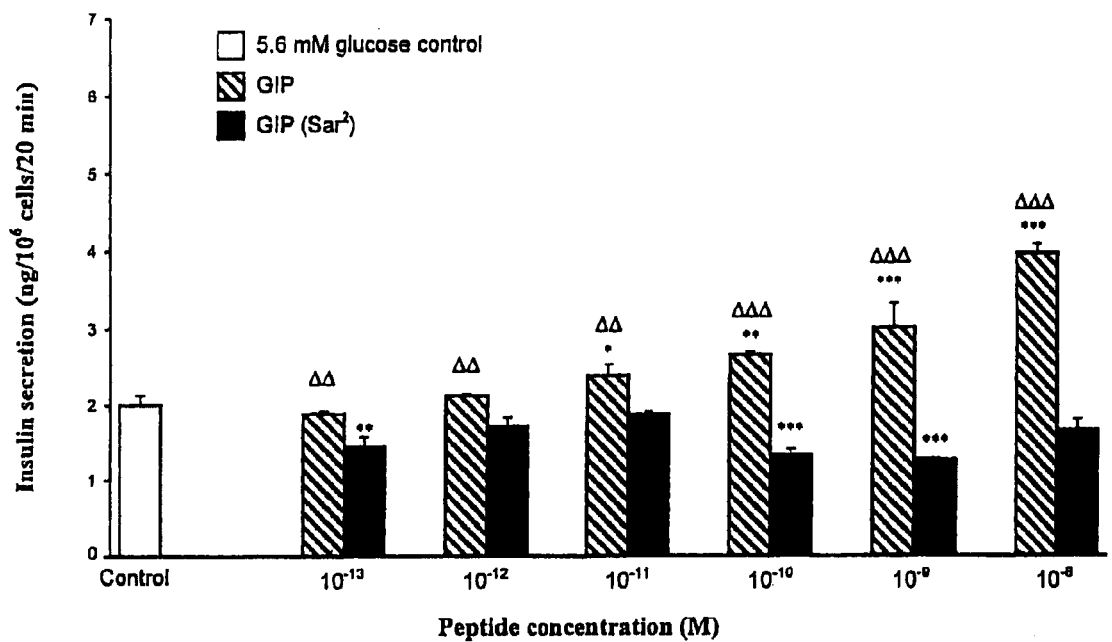
Fig.19. Graph showing the effects of various concentrations of GIP and GIP (Sar$^2$) on insulin release from BRIN-BD11 cells incubated at 5.6 mM glucose
Values are means ± S.E.M. for 12 separate observations. $^*P< 0.05$, $^{}P< 0.01$, $^{*}P<0.001$ compared to control (5.6mM glucose alone). $^{\Delta}P<0.05$, $^{\Delta\Delta}P<0.01$, $^{\Delta\Delta\Delta}P<0.001$ compared to GIP (Sar$^2$) at the same concentration.

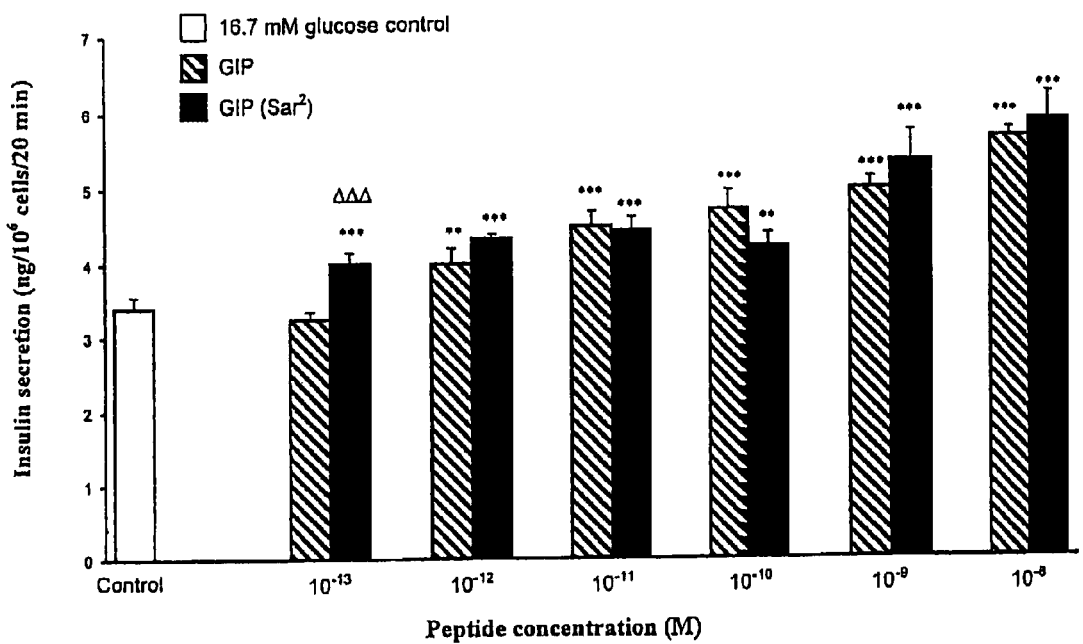
Fig. 20. Graph showing the effects of various concentrations of GIP and GIP (Sar$^2$) on insulin release from BRIN-BD11 cells incubated at 16.7 mM glucose
Values are means ± S.E.M. for 12 separate observations. *P< 0.05, P< 0.01, *P<0.001 compared to control (16.7 mM glucose alone). $^\Delta$P<0.05, $^{\Delta\Delta}$P<0.01, $^{\Delta\Delta\Delta}$P<0.001 compared to GIP (Sar$^2$) at the same concentration.

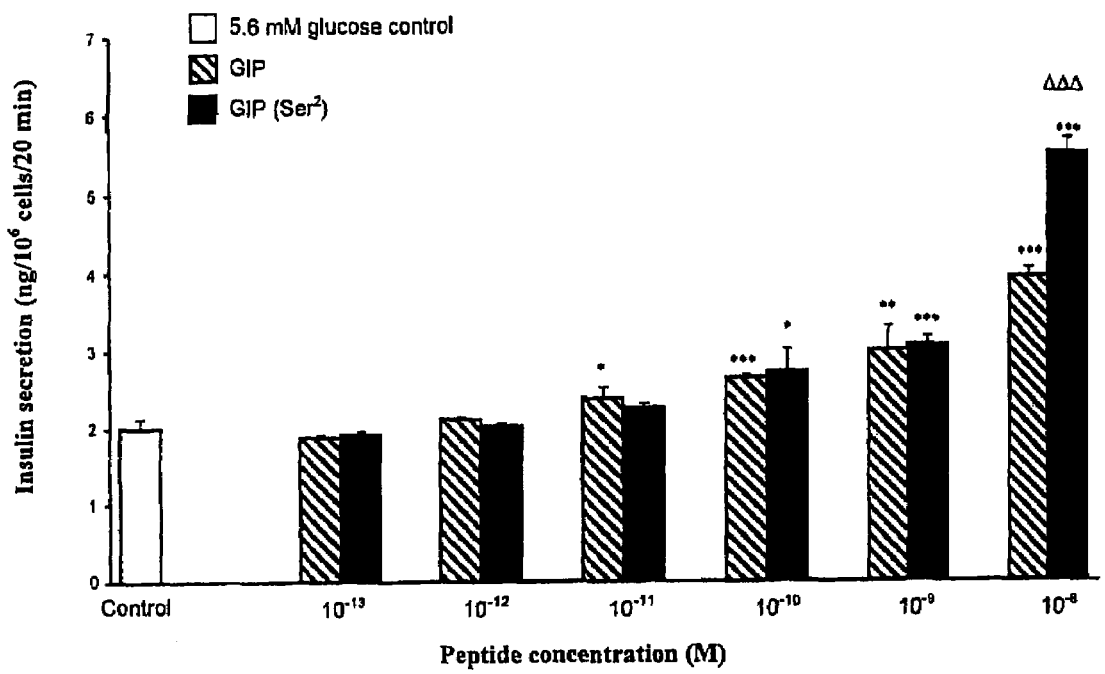
Fig.21. Graph showing the effects of various concentrations of GIP and GIP (Ser$^2$) on insulin release from BRIN-BD11 cells incubated at 5.6 mM glucose
Values are means ± S.E.M. for 12 separate observations. $^*P<0.05$, $^{}P<0.01$, $^{*}P<0.001$ compared to control (5.6mM glucose alone). $^{\Delta}P<0.05$, $^{\Delta\Delta}P<0.01$, $^{\Delta\Delta\Delta}P<0.001$ compared to GIP (Ser$^2$) at the same concentration.

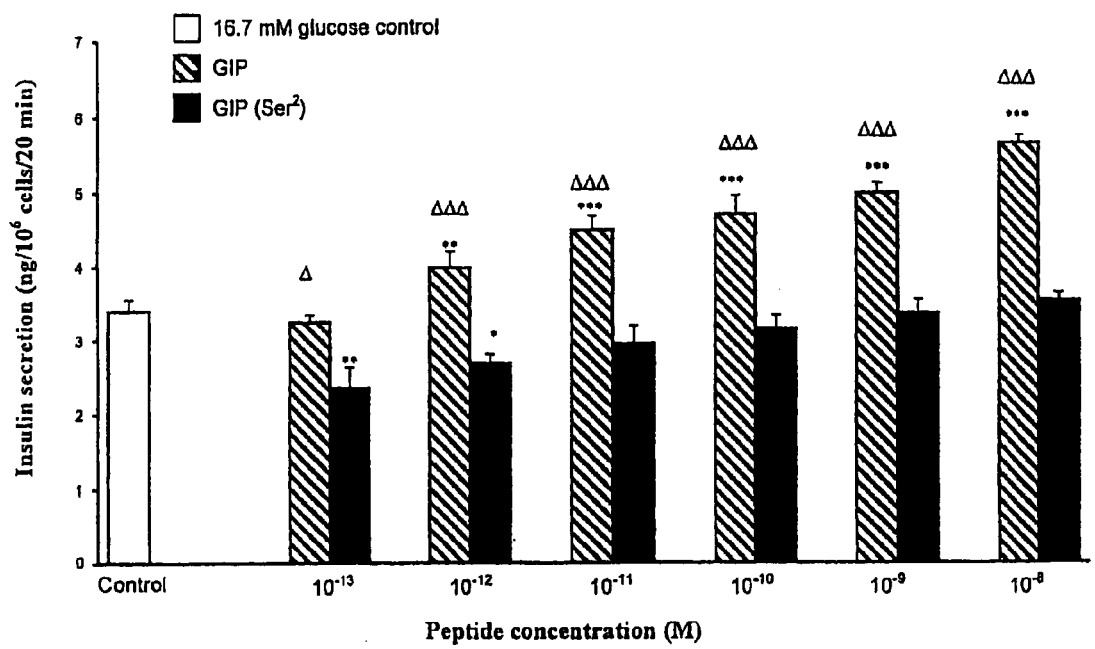
Fig. 22. Graph showing the effects of various concentrations of GIP and GIP (Ser$^2$) on insulin release from BRIN-BD11 cells incubated at 16.7 mM glucose
Values are means ± S.E.M. for 12 separate observations. $^*P< 0.05$, $^{}P< 0.01$, $^{*}P<0.001$ compared to control (16.7 mM glucose alone). $^\Delta P<0.05$, $^{\Delta\Delta}P<0.01$, $^{\Delta\Delta\Delta}P<0.001$ compared to GIP (Ser$^2$) at the same concentration.

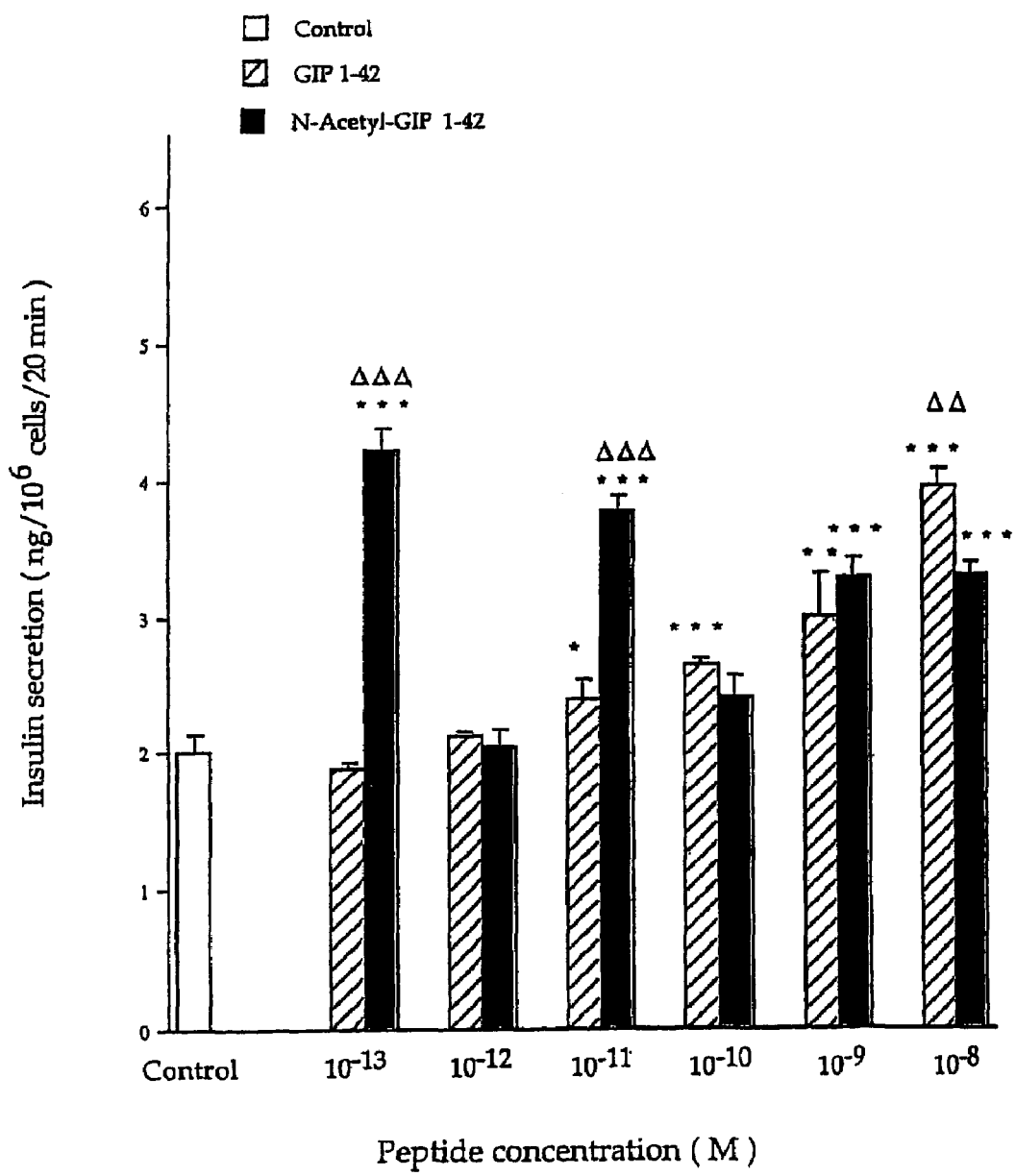
Fig. 23 Graph showing the effects of various concentrations of GIP 1-42 and N-Acetyl-GIP 1-42 on insulin release from BRIN-BD11 cells incubated at 5.6 mM glucose

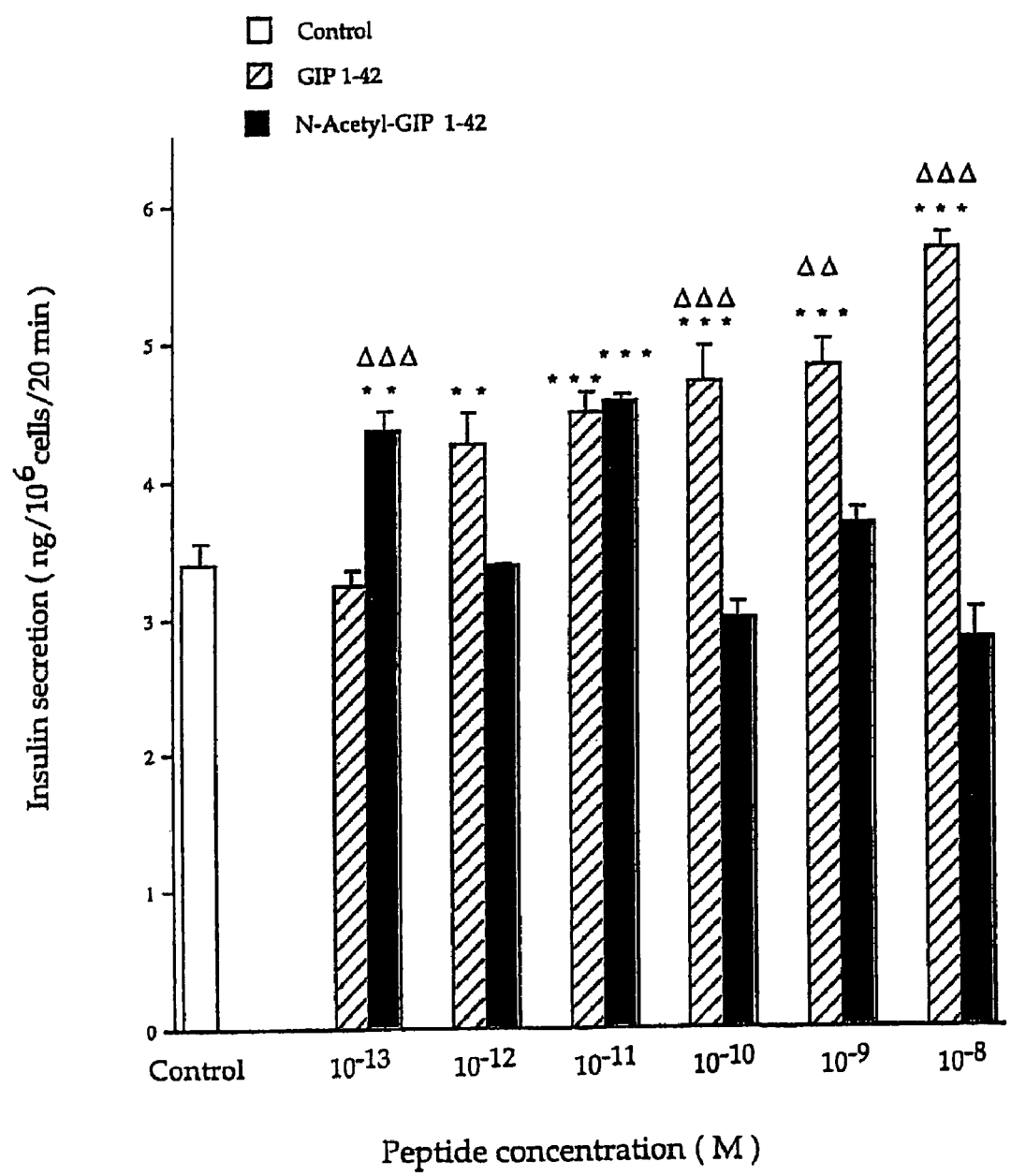
Fig. 24 Graph showing the effects of various concentrations of GIP 1-42 and N-Acetyl-GIP 1-42 on insulin release from BRIN-BD11 cells incubated at 16.7 mM glucose

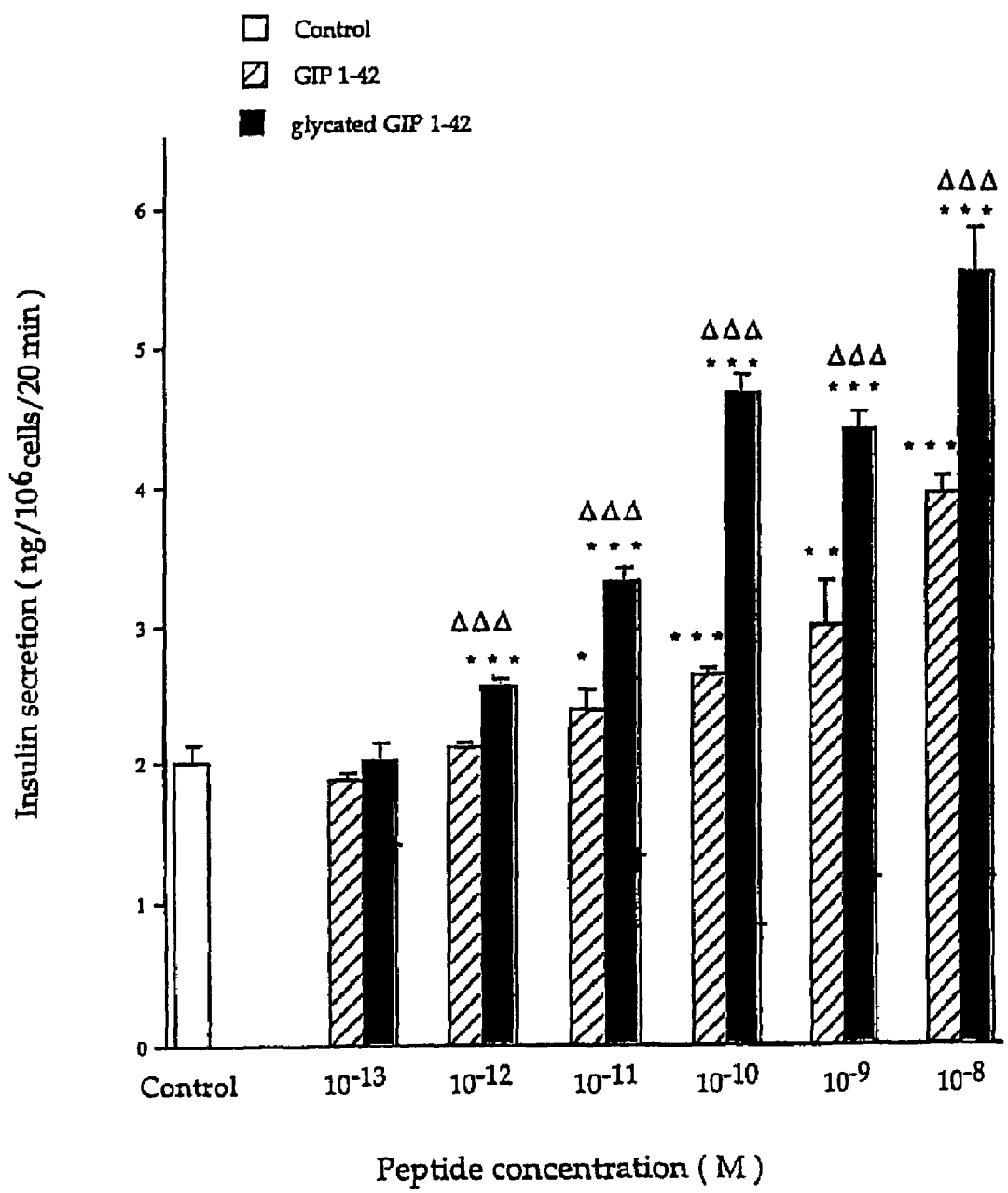
Fig. 25 Graph showing the effects of various concentrations of GIP 1-42 and glycated GIP 1-42 on insulin release from BRIN-BD11 cells incubated at 5.6 mM glucose

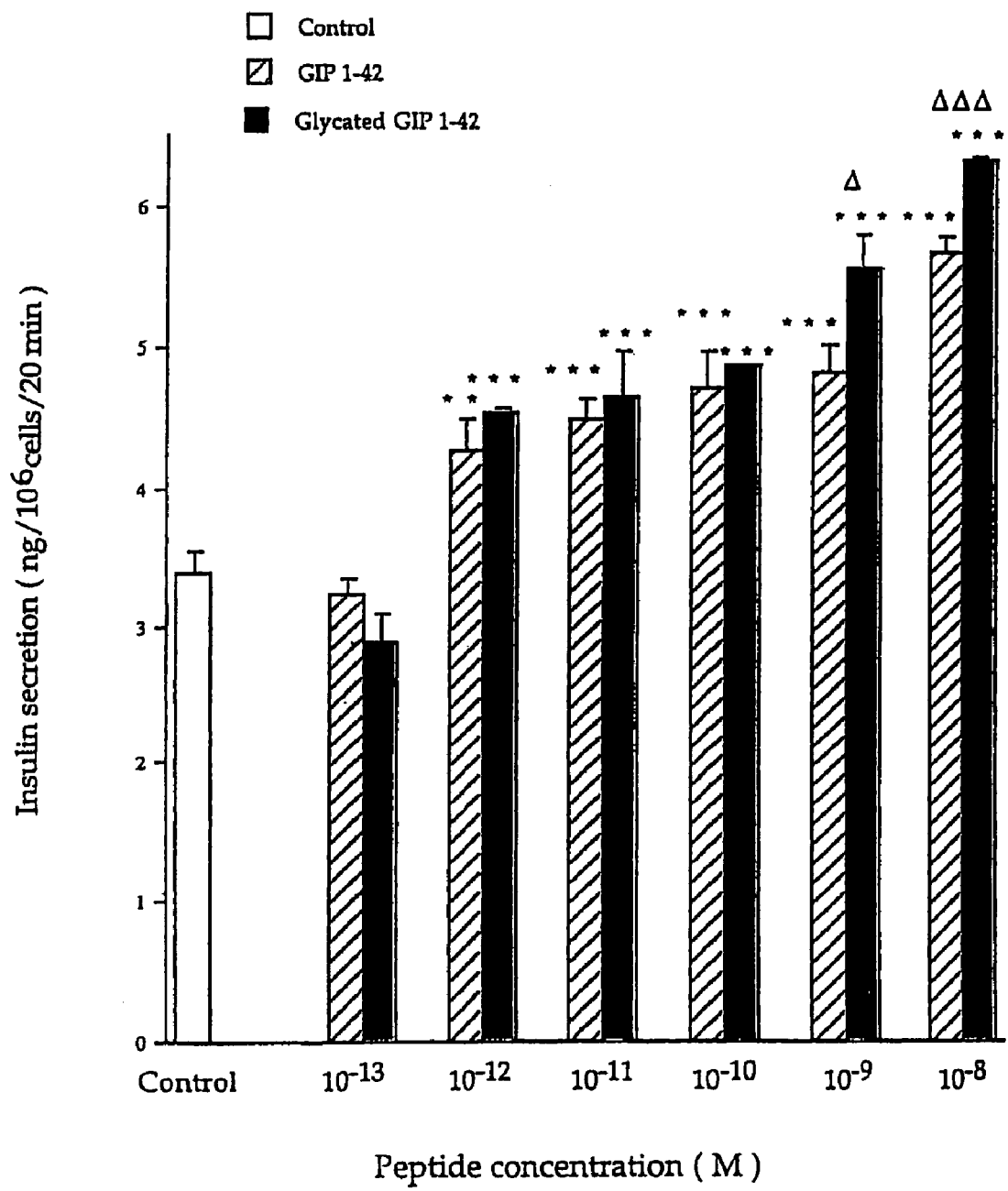
Fig. 26 Graph showing the effects of various concentrations of GIP 1-42 and glycated GIP 1-42 on insulin release from BRIN-BD11 cells incubated at 16.7 mM glucose

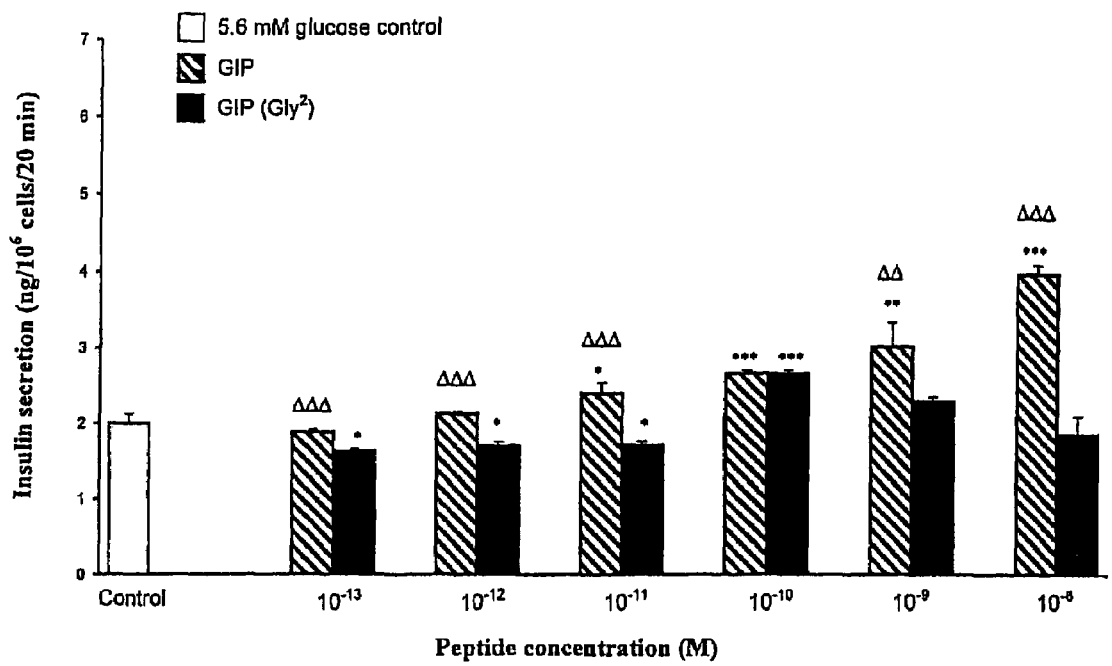
Fig. 27 Graph showing the effects of various concentrations of GIP and GIP (Gly$^2$) on insulin release from BRIN-BD11 cells incubated at 5.6 mM glucose
Values are means ± S.E.M. for 12 separate observations. *P< 0.05, P< 0.01, *P<0.001 compared to control (5.6mM glucose alone). ᐃP<0.05, ᐃᐃP<0.01, ᐃᐃᐃP<0.001 compared to GIP (Gly$^2$) at the same concentration.

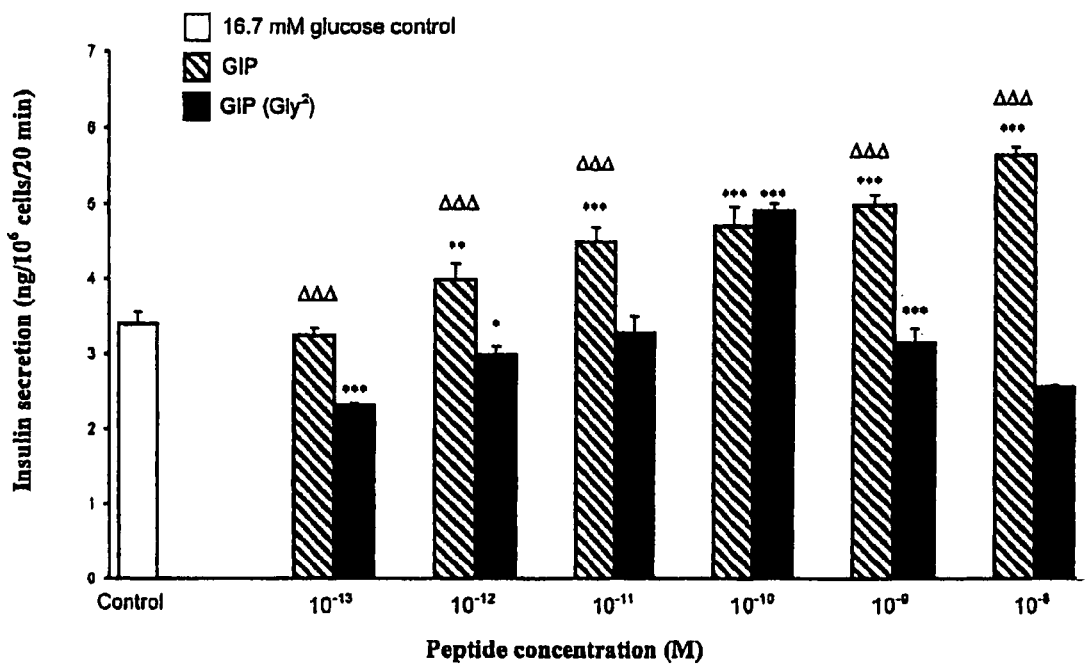
Fig. 28 Graph showing the effects of various concentrations of GIP and GIP (Gly$^2$) on insulin release from BRIN-BD11 cells incubated at 16.7 mM glucose
Values are means ± S.E.M. for 12 separate observations. $^*P< 0.05$, $^{}P< 0.01$, $^{*}P<0.001$ compared to control (16.7 mM glucose alone). $^{\Delta}P<0.05$, $^{\Delta\Delta}P<0.01$, $^{\Delta\Delta\Delta}P<0.001$ compared to GIP (Gly$^2$) at the same concentration.

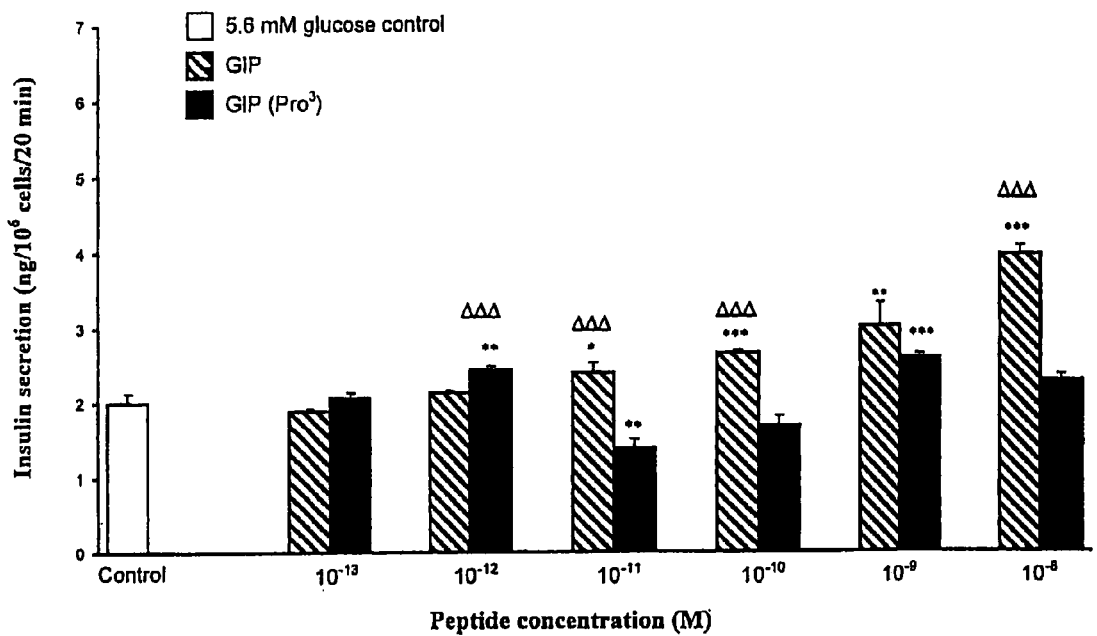
Fig. 29 Graph showing the effects of various concentrations of GIP and GIP (Pro$^3$) on insulin release from BRIN-BD11 cells incubated at 5.6 mM glucose
Values are means ± S.E.M. for 12 separate observations. *P< 0.05, P< 0.01, *P<0.001 compared to control (5.6mM glucose alone). $^\Delta$P<0.05, $^{\Delta\Delta}$P<0.01, $^{\Delta\Delta\Delta}$P<0.001 compared to GIP (Pro$^3$) at the same concentration.

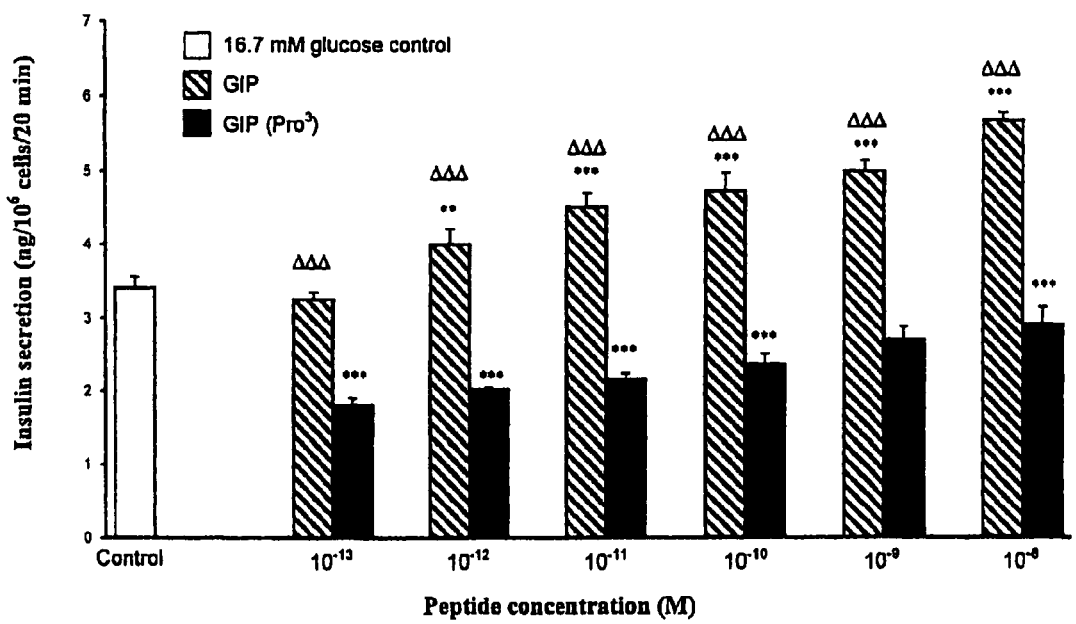
Fig. 30 Graph showing the effects of various concentrations of GIP and GIP (Pro$^3$) on insulin release from BRIN-BD11 cells incubated at 16.7 mM glucose
Values are means ± S.E.M. for 12 separate observations. $^*P< 0.05$, $^{}P< 0.01$, $^{*}P<0.001$ compared to control (16.7 mM glucose alone). $^{\Delta}P<0.05$, $^{\Delta\Delta}P<0.01$, $^{\Delta\Delta\Delta}P<0.001$ compared to GIP (Pro$^3$) at the same concentration.

SEQUENCE LISTING

<160> NUMBER OF SEQ ID NOS: 2

<210> SEQ ID NO 1
<211> LENGTH: 42
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 42
<212> TYPE: PRT
<213> ORGANISM: Pig

<400> SEQUENCE: 2

Tyr Ala Glu Gly Thr Phe Ile Ser Asp Tyr Ser Ile Ala Met Asp Lys
1               5                   10                  15

```
Ile Arg Gln Gln Asp Phe Val Asn Trp Leu Leu Ala Gln Lys Gly Lys
            20                  25                  30

Lys Ser Asp Trp Lys His Asn Ile Thr Gln
        35                  40
```

ANALOGS OF GASTRIC INHIBITORY POLYPEPTIDE AND THEIR USE OF TREATMENT FOR DIABETES

CROSS REFERENCE TO RELATED APPLICATIONS

This application is continuation of U.S. application Ser. No. 09/937,687, filed Jan. 8, 2002, now U.S. Pat. No. 6,921,748, which is the U.S. National Phase Application of International Application No. PCT/GB00/01089, which designated the United States and was filed on Mar. 29, 2000 and published in English, which in turn claims the benefit of GB9907216.7, filed on Mar. 29, 1999, and GB9917565.5, filed Jul. 27, 1999. The entire teachings of the above applications are incorporated herein by reference.

The present invention relates to the release of insulin and the control of blood glucose concentration. More particularly the invention relates to the use of peptides to stimulate release of insulin, lowering of blood glucose and pharmaceutical preparations for treatment of type 2 diabetes.

Gastric inhibitory polypeptide (GIP) and glucagon-like peptide-1(7-36)amide (truncated GLP-1; tGLP-1) are two important insulin-releasing hormones secreted from endocrine cells in the intestinal tract in response to feeding. Together with autonomic nerves they play a vital supporting role to the pancreatic islets in the control of blood glucose homeostasis and nutrient metabolism.

Dipeptidyl peptidase IV (DPP IV; EC 3.4.14.5) has been identified as a key enzyme responsible for inactivation of GIP and tGLP-1 in serum. DPP IV is completely inhibited in serum by the addition of diprotin A(DPA, 0.1 mmol/l). This occurs through the rapid removal of the N-terminal dipeptides $Tyr^1$-$Ala^2$ and $His^7$-$Ala^8$ giving rise to the main metabolites GIP(3-42) and GLP-1(9-36)amide, respectively. These truncated peptides are reported to lack biological activity or to even serve as antagonists at GIP or tGLP-1 receptors. The resulting biological half-lives of these incretin hormones in vivo are therefore very short, estimated to be no longer than 5 min.

In situations of normal glucose regulation and pancreatic B-cell sensitivity, this short duration of action is advantageous in facilitating momentary adjustments to homeostatic control. However, the current goal of a possible therapeutic role of incretin hormones, particularly tGLP-1 in NIDDM therapy is frustrated by a number of factors in addition to finding a convenient route of administration. Most notable of these are rapid peptide degradation and rapid absorption (peak concentrations reached 20 min) and the resulting need for both high dosage and precise timing with meals. Recent therapeutic strategies have focused on precipitated preparations to delay peptide absorption and inhibition of GLP-1 degradation using specific inhibitors of DPP IV. A possible therapeutic role is also suggested by the observation that a specific inhibitor of DPP IV, isoleucine thiazolidide, lowered blood glucose and enhanced insulin secretion in glucose-treated diabetic obese Zucker rats presumably by protecting against catabolism of the incretin hormones tGLP-1 and GIP.

Numerous studies have indicated that tGLP-1 infusion restores pancreatic B-cell sensitivity, insulin secretory oscillations and improved glycemic control in various groups of patients with IGT or NIDDM. Longer term studies also show significant benefits of tGLP-1 injections in NIDDM and possibly IDDM therapy, providing a major incentive to develop an orally effective or long-acting tGLP-1 analogue. Several attempts have been made to produce structurally modified analogues of tGLP-1 which are resistant to DPP IV degradation. A significant extension of serum half-life is observed with $His^7$-glucitol tGLP-1 and tGLP-1 analogues substituted at position 8 with Gly, Aib, Ser or Thr. However, these structural modifications seem to impair receptor binding and insulinotrophic activity thereby compromising part of the benefits of protection from proteolytic degradation. In recent studies using $His^7$-glucitol tGLP-1, resistance to DPP IV and serum degradation was accompanied by severe loss of insulin-releasing activity.

GIP shares not only the same degradation pathway as tGLP-1 but many similar physiological actions, including stimulation of insulin and somatostatin secretion, and the enhancement of glucose disposal. These actions are viewed as key aspects in the antihyperglycemic properties of tGLP-1, and there is therefore good expectation that GIP may have similar potential as NIDDM therapy. Indeed, compensation by GIP is held to explain the modest disturbances of glucose homeostasis observed in tGLP-1 knockout mice. Apart from early studies, the anti-diabetic potential of GIP has not been explored and tGLP-1 may seem more attractive since it is viewed by some as a more potent insulin secretagogue when infused at "so called" physiological concentrations estimated by RIA.

The present invention aims to provide effective analogues of GIP. It is one aim of the invention to provide a pharmaceutical for treatment of Type 2 diabetes.

According to the present invention there is provided an effective peptide analogue of the biologically active GIP(1-42) which has improved characteristics for treatment of Type 2 diabetes wherein the analogue comprises at least 15 amino acid residues from the N terminus of GIP(1-42) and has at least one amino acid substitution or modification at position 1-3 and not including $Tyr^1$ glucitol GIP(1-42).

The structures of human and porcine GIP(1-42) are shown below. The porcine peptide differs by just two amino acid substitutions at positions 18 and 34.

The analogue may include modification by fatty acid addition at an epsilon amino group of at least one lysine residue.

The invention includes $Tyr^1$ glucitol GIP(1-42) having fatty acid addition at an epsilon amino group of at least one lysine residue.

Primary structure of human gastric inhibitory polypeptide (GIP)

```
                                           (SEQ ID NO:1)
       1               5                10
NH2-Tyr-Ala-Glu-Gly-Thr-Phe-Ile-Ser-Asp-Tyr-Ser- 15                  20
Ile-Ala-Met-Asp-Lys-Ile-His-Gln-Gln-Asp-Phe-Val- 25                  30                  35
Asn-Trp-Leu-Leu-Ala-Gln-Lys-Gly-Lys-Lys-Asn-Asp-

40
Trp-Lys-His-Asn-Ile-Thr-Gln-COOH
```

Primary structure of porcine gastric inhibitory polypeptide (GIP)

```
                                           (SEQ ID NO:2)
       1               5                10
NH2-Tyr-Ala-Glu-Gly-Thr-Phe-Ile-Ser-Asp-Tyr-Ser- 15                  20
Ile-Ala-Met-Asp-Lys-Ile-Arg-Gln-Gln-Asp-Phe-Val-
```

-continued

```
            25              30              35
Asn-Trp-Leu-Leu-Ala-Gln-Lys-Gly-Lys-Lys-Ser-Asp-

40
Trp-Lys-His-Asn-Ile-Thr-Gln-COOH
```

Analogues of GIP(1-42) may have an enhanced capacity to stimulate insulin secretion, enhance glucose disposal, delay glucose absorption or may exhibit enhanced stability in plasma as compared to native GIP. They also may have enhanced resistance to degradation.

Any of these properties will enhance the potency of the analogue as a therapeutic agent.

Analogues having D-amino acid substitutions in the 1, 2 and 3 positions and/or N-glycated, N-alkylated, N-acetylated or N-acylated amino acids in the 1 position are resistant to degradation in vivo.

Various amino acid substitutions at second and third amino terminal residues are included, such as GIP(1-42) Gly2, GIP(1-42)Ser2, GIP(1-42)Abu2, GIP(1-42)Aib, GIP(1-42)D-Ala2, GIP(1-42)Sar2, and GIP(1-42)Pro3.

Amino-terminally modified GIP analogues include N-glycated GIP(1-42), N-alkylated GIP(1-42), N-acetylated GIP(1-42) and N-isopropyl GIP(1-42).

Other stabilised analogues include those with a peptide isostere bond between amino terminal residues at position 2 and 3. These analogues may be resistant to the plasma enzyme dipeptidyl-peptidase IV (DPP IV) which is largely responsible for inactivation of GIP by removal of the amino-terminal dipeptide Tyr1-Ala2.

In particular embodiments, the invention provides a peptide which is more potent than human or porcine GIP in moderating blood glucose excursions, said peptide consisting of GIP(1-42) or N-terminal fragments of GIP(1-42) consisting of up to between 15 to 30 amino acid residues from the N-terminus (i.e., GIP(1-15) through GIP(1-30)) with one or more modifications selected from the group consisting of:

(a) substitution of $Ala^2$ by Gly
(b) substitution of $Ala^2$ by Ser
(c) substitution of $Ala^2$ by Abu
(d) substitution of $Ala^2$ by Aib
(e) substitution of $Ala^2$ by D-Ala
(f) substitution of $Ala^2$ by Sar
(g) substitution of $Glu^3$ by Pro
(h) modification of $Tyr^1$ by acetylation
(i) modification of $Tyr^1$ by acylation
(j) modification of $Tyr^1$ by alkylation
(k) modification of $Tyr^1$ by glycation
(l) conversion of $Ala^2$-$Glu^3$ bond to a psi [$CH_2NH$] bond
(m) conversion of $Ala^2$-$Glu^3$ bond to a stable peptide isostere bond
(n) (n-isopropyl-H) 1GIP.

The invention also provides the use of $Tyr^1$-glucitol GIP in the preparation of a medicament for the treatment of diabetes.

The invention further provides improved pharmaceutical compositions including analogues of GIP with improved pharmacological properties.

Other possible analogues include certain commonly encountered amino acids, which are not encoded by the genetic code, for example, beta-alanine (beta-ala), or other omega-amino acids, such as 3-amino propionic, 4-amino butyric and so forth, ornithine (Orn), citrulline (Cit), homoarginine (Har), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) and methionine sulfoxide (MSO), substitution of the D form of a neutral or acidic amino acid or the D form of tyrosine for tyrosine.

According to the present invention there is also provided a pharmaceutical composition useful in the treatment of diabetes type II which comprises an effective amount of the peptide as described herein, in admixture with a pharmaceutically acceptable excipient.

The invention also provides a method of N-terminally modifying GIP or analogues thereof the method comprising the steps of synthesizing the peptide from the C terminal to the penultimate N terminal amino acid, adding tyrosine to a bubbler system as a F-moc protected Tyr(tBu)-Wang resin, deprotecting the N-terminus of the tyrosine and reacting with the modifying agent, allowing the reaction to proceed to completion, cleaving the modified tyrosine from the Wang resin and adding the modified tyrosine to the peptide synthesis reaction.

Preferably the agent is glucose, acetic anhydride or pyroglutamic acid.

The invention will now be demonstrated with reference to the following non-limiting example and the accompanying figures wherein:

FIG. 5 shows effects of GIP on plasma insulin responses.

FIG. 6 illustrates DPP-IV degradation of GIP 1-42.

FIG. 7 illustrates DPP-IV degradation of GIP ($Abu^2$).

FIG. 8 illustrates DPP-IV degradation of GIP ($Sar^2$).

FIG. 9 illustrates DPP-IV degradation of GIP ($Ser^2$),

FIG. 10 illustrates DPP-IV degradation of N-Acetyl-GIP.

FIG. 11 illustrates DPP-IV degradation of glycated GIP.

FIG. 12 illustrates human plasma degradation of GIP.

FIG. 13 illustrates human plasma degradation of GIP ($Abu^2$).

FIG. 14 illustrates human plasma degradation of GIP ($Sar^2$)

FIG. 15 illustrates human plasma degradation of GIP ($Ser^2$)

FIG. 16 illustrates human plasma degradation of glycated GIP.

FIG. 17 shows the effects of various concentrations of GIP 1-42 and GIP ($Abu^2$) on insulin release from BRIN-BD11 cells incubated at 5.6 mM glucose.

FIG. 18 shows the effects of various concentrations of GIP 1-42 and GIP ($Abu^2$) on insulin release from BRIN-BD11 cells incubated at 16.7 mM glucose.

FIG. 19 shows the effects of various concentrations of GIP 1-42 and GIP ($Sar^2$) on insulin release from BRIN-BD11 cells incubated at 5.6 mM glucose.

FIG. 20 shows the effects of various concentrations of GIP 1-42 and GIP ($Sar^2$) on insulin release from BRIN-BD11 cells incubated at 16.7 mM glucose.

FIG. 21 shows the effects of various concentrations of GIP 1-42 and GIP ($Ser^2$) on insulin release from BRIN-BD11 cells incubated at 5.6 mM glucose.

FIG. 22 shows the effects of various concentrations of GIP 1-42 and GIP (Ser$^2$) on insulin release from BRIN-BD11 cells incubated at 16.7 mM glucose.

FIG. 23 shows the effects of various concentrations of GIP 1-42 and N-Acetyl-GIP 1-42 on insulin release from BRIN-BD11 cells incubated at 5.6 mM glucose.

FIG. 24 shows the effects of various concentrations of GIP 1-42 and N-Acetyl-GIP 1-42 on insulin release from BRIN-BD11 cells incubated at 16.7 mM glucose.

FIG. 25 shows the effects of various concentrations of GIP 1-42 and glycated GIP 1-42 on insulin release from BRIN-BD11 cells incubated at 5.6 mM glucose.

FIG. 26 shows the effects of various concentrations of GIP 1-42 and glycated GIP 1-42 on insulin release from BRIN-BD11 cells incubated at 16.7 mM glucose.

FIG. 27 shows the effects of various concentrations of GIP 1-42 and GIP (Gly$^2$) on insulin release from BRIN-BD11 cells incubated at 5.6 mM glucose.

FIG. 28 shows the effects of various concentrations of GIP 1-42 and GIP (Gly$^2$) on insulin release from BRIN-BD11 cells incubated at 16.7 mM glucose.

FIG. 29 shows the effects of various concentrations of GIP 1-42 and GIP (Pro$^3$) on insulin release from BRIN-BD11 cells incubated at 5.6 mM glucose.

FIG. 30 shows the effects of various concentrations of GIP 1-42 and GIP (Pro$^3$) on insulin release from BRIN-BD11 cells incubated at 16.7 mM glucose.

EXAMPLE 1

Figure 1A:
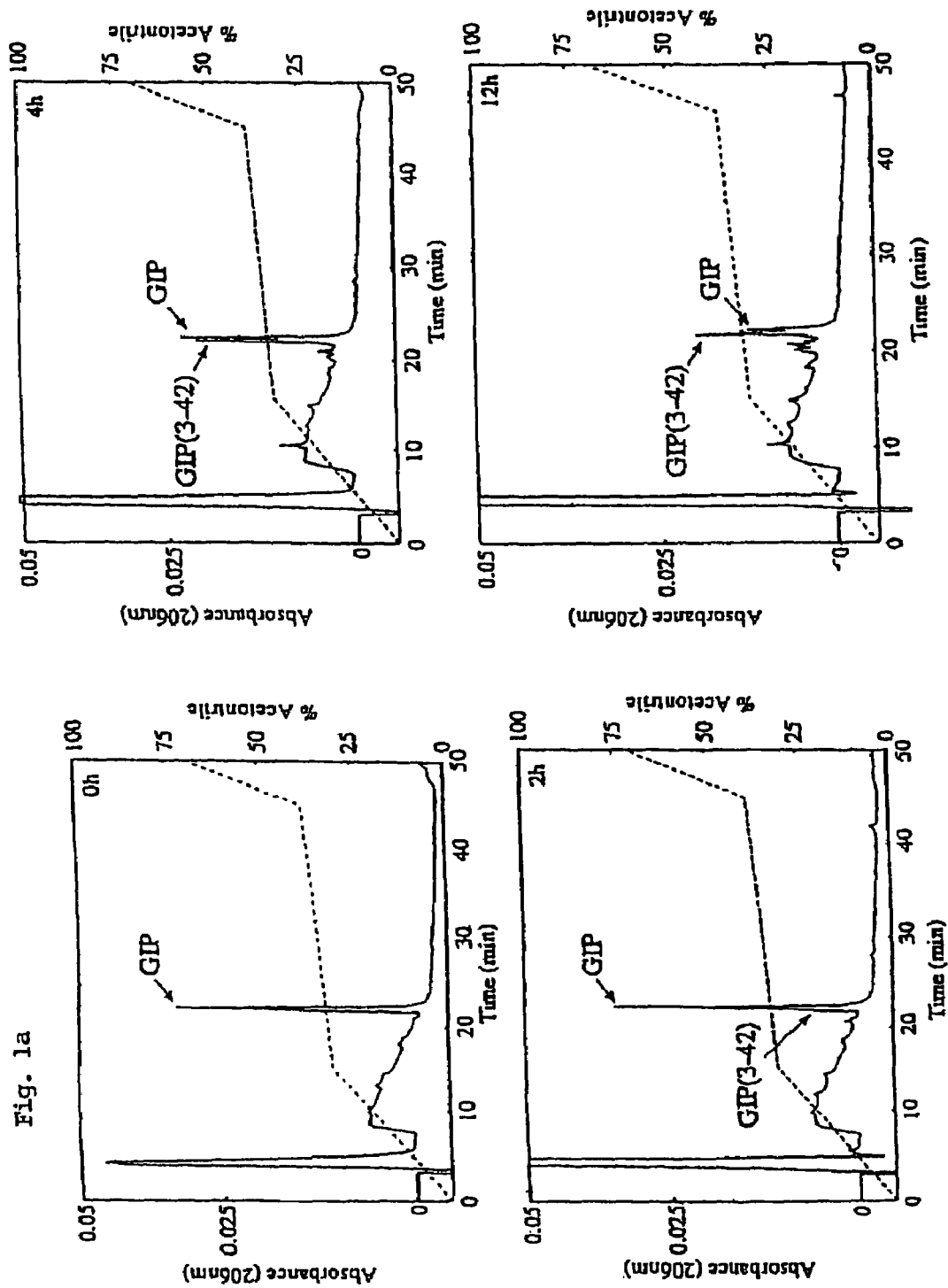
FIG. 1a illustrates degradation of GIP by DPP IV.

Preparation of N-terminally Modified GIP and Analogues Thereof

The N-terminal modification of GIP is essentially a three step process. Firstly, GIP is synthesized from its C-terminus (starting from a Fmoc-Gln (Trt)-Wang resin, Novabiochem) up to the penultimate N-terminal amino-acid (Ala$^2$) on an automated peptide synthesizer (Applied Biosystems, Calif., USA). The synthesis follows standard Fmoc peptide chemistry protocols. Secondly, the N-terminal amino-acid of native GIP (Tyr) is added to a manual bubbler system as a Fmoc-protected Tyr(tBu)-Wang resin. This amino acid is deprotected at its N-terminus (piperidine in DMF (20% v/v)) and allowed to react with a high concentration of glucose (glycation, under reducing conditions with sodium cyanoborohydride), acetic anhydride (acetylation), pyroglutamic acid (pyroglutamyl) etc. for up to 24 h as necessary to allow the reaction to go to completion. The completeness of reaction will be monitored using the ninhydrin test which will determine the presence of available free α-amino groups. Thirdly, (once the reaction is complete) the now structurally modified Tyr is cleaved from the wang resin (95% TFA, and 5% of the appropriate scavengers. N.B. Tyr is considered to be a problematic amino acid and may need special consideration) and the required amount of N-terminally modified-Tyr consequently added directly to the automated peptide synthesizer, which will carry on the synthesis, thereby stitching the N-terminally modified-Tyr to the α-amino of GIP (Ala$^2$), completing the synthesis of the GIP analogue. This peptide is cleaved off the Wang resin (as above) and then worked up using the standard Buchner filtering, precipitation, rotary evaporation and drying techniques.

EXAMPLE 2

The following example investigates preparation of Tyr$^1$-glycitol GIP together with evaluation of its antihyperglycemic and insulin-releasing properties in vivo. The results clearly demonstrate that this novel GIP analogue exhibits a substantial resistance to aminopeptidase degradation and increased glucose lowering activity compared with the native GIP.

Research Design and Methods

Materials. Human GIP was purchased from the American Peptide Company (Sunnyvale, Calif., USA). HPLC grade acetonitrile was obtained from Rathburn (Walkersburn, Scotland). Sequencing grade trifluoroacetic acid (TFA) was obtained from Aldrich (Poole, Dorset, UK). All other chemicals purchased including dextran T-70, activated charcoal, sodium cyanoborohydride and bovine serum albumin fraction V were from Sigma (Poole, Dorset, UK). Diprotin A (DPA) was purchased from Calbiochem-Novabiochem (UK) Ltd. (Beeston, Nottingham, UK) and rat insulin standard for RIA was obtained form Novo Industria (Copenhagen, Denmark). Reversed-phase Sep-Pak cartridges (C-18) were purchased from Millipore-Waters (Milford, Mass., USA). All water used in these experiments was purified using a Milli-Q, Water Purification System (Millipore Corporation, Milford, Mass., USA).

Preparation of Tyr$^1$-glucitol GIP. Human GIP was incubated with glucose under reducing conditions in 10 mmol/l sodium phosphate buffer at pH 7.4 for 24 h. The reaction was stopped by addition of 0.5 mol/l acetic acid (30 μl) and the mixture applied to a Vydac (C-18)(4.6×250 mm) analytical HPLC column (The Separations Group, Hesperia, Calif., USA) and gradient elution conditions were established using aqueous/TFA and acetonitrile/TFA solvents. Fractions corresponding to the glycated peaks were pooled, taken to dryness under vacuum using an AES 1000 Speed-Vac concentrator (Life Sciences International, Runcorn, UK) and purified to homogeneity on a Supelcosil (C-8) (4.6×150 mm) column (Supelco Inc., Poole, Dorset, UK).

Degradation of GIP and Tyr$^1$-glucitol GIP by DPP IV. HPLC-purified GIP or Tyr$^1$-glucitol GIP were incubated at 37° C. with DPP-IV (5 mU) for various time periods in a reaction mixture made up to 500 μl with 50 mmol/l triethanolamine-HCl, pH 7.8 (final peptide concentration 1 μmol/l). Enzymatic reactions were terminated after 0, 2, 4 and 12 hours by addition of 5 μl of 10% (v/v) TFA/water. Samples were made up to a final volume of 1.0 ml with 0.12% (v/v) TFA and stored at −20° C. prior to HPLC analysis.

Degradation of GIP and Tyr$^1$-glucitol GIP by human plasma. Pooled human plasma (20 μl) taken from six healthy fasted human subjects was incubated at 37° C. with GIP or Tyr$^1$-glucitol GIP (10 μg) for 0 and 4 hours in a reaction mixture made up to 500 μl, containing 50 mmol/l triethanolamine/HCL buffer pH 7.8. Incubations for 4 hours were also performed in the presence of diprotin A (5 mU). The reactions were terminated by addition of 5 μl of TFA and the final volume adjusted to 1.0 ml using 0.1% v/v TFA/water. Samples were centrifuged (13,000 g, 5 min) and the supernatant applied to a C-18 Sep-Pak cartridge (Millipore-Waters) which was previously primed and washed with 0.1% (v/v) TFA/water. After washing with 20 ml 0.12% TFA/water, bound material was released by elution with 2 ml of 80% (v/v) acetonitrile/water and concentrated using a Speed-Vac concentrator (Runcorn, UK). The volume was adjusted to 11.0 ml with 0.12% (v/v) TFA/water prior to HPLC purification.

HPLC analysis of degraded GIP and Tyr$^1$-glucitol GIP. Samples were applied to a Vydac C-18 widepore column equilibrated with 0.12% (v/v) TFA/H$_2$O at a flow rate of 1.0 ml/min. Using 0.1% (v/v) TFA in 70% acetonitrile/H$_2$O, the concentration of acetonitrile in the eluting solvent was raised from 0% to 31.5% over 15 min, to 38.5% over 30 min and from 38.5% to 70% over 5 min, using linear gradients. The absorbance was monitored at 206 nm and peak areas evaluated using a model 2221 LKB integrator. Samples recovered manually were concentrated using a Speed-Vac concentrator.

Electrospray ionization mass spectrometry (ESI-MS). Samples for ESI-MS analysis containing intact and degradation fragments of GIP (from DPP IV and plasma incubations) as well as Tyr$^1$-glucitol GIP, were further purified by HPLC. Peptides were dissolved (approximately 400 pmol) in 100 µl of water and applied to the LCQ benchtop mass spectrometer (Finnigan MAT, Hemel Hempstead, UK) equipped with a microbore C-18 HPLC column (150×2.0 mm, Phenomenex, UK, Ltd, Macclesfield). Samples (30 µl direct loop injection) were injected at a flow rate of 0.2 ml/min, under isocratic conditions 35% (v/v) acetonitrile/water. Mass spectra were obtained from the quadripole ion trap mass analyzer and recorded. Spectra were collected using full ion scan mode over the mass-to-charge (m/z) range 150-2000. The molecular masses of GIP and related structures were determined from ESI-MS profiles using prominent multiple charged ions and the following equation $M_r=iM_i$, (where $M_r$=molecular mass; $M_i$=m/z ratio; i=number of charges; $M_h$=mass of a proton).

In vivo biological activity of GIP and Tyr$^1$-glucitol GIP. Effects of GIP and Tyr$^1$-glucitol GIP on plasma glucose and insulin concentrations were examined using 10-12 week old male Wistar rats. The animals were housed individually in an air conditioned room and 22±2° C. with a 12 hour light/12 hour dark cycle. Drinking water and a standard rodent maintenance diet (Trouw Nutrition, Cheshire, UK) were supplied ad libitum. Food was withdrawn for an 18 hour period prior to intraperitoneal injection of glucose alone (18 mmol/kg body weight) or in combination with either GIP or Tyr$^1$-glucitol GIP (10 nmol/kg). Test solutions were administered in a final volume of 8 ml/kg body weight. Blood samples were collected at 0, 15, 30 and 60 minutes from the cut tip of the tail of conscious rats into chilled fluoride/heparin microcentrifuge tubes (Sarstedt, Nümbrecht, Germany). Samples were centrifuged using a Beckman microcentrifuge for about 30 seconds at 13,000 g. Plasma samples were aliquoted and stored at −20° C. prior to glucose and insulin determinations. All animal studies were done in accordance with the Animals (Scientific Procedures) Act 1986.

Analyses. Plasma glucose was assayed by an automated glucose oxidase procedure using a Beckman Glucose Analyzer II [33]. Plasma insulin was determined by dextran charcoal radioimmunoassay as described previously [34]. Incremental areas under plasma glucose and insulin curves (AUC) were calculated using a computer program (CAREA) employing the trapezoidal rule [35] with baseline subtraction. Results are expressed as mean±SEM and values were compared using the Student's unpaired t-test. Groups of data were considered to be significantly different if P<0.05.

Results

Figure 1B:
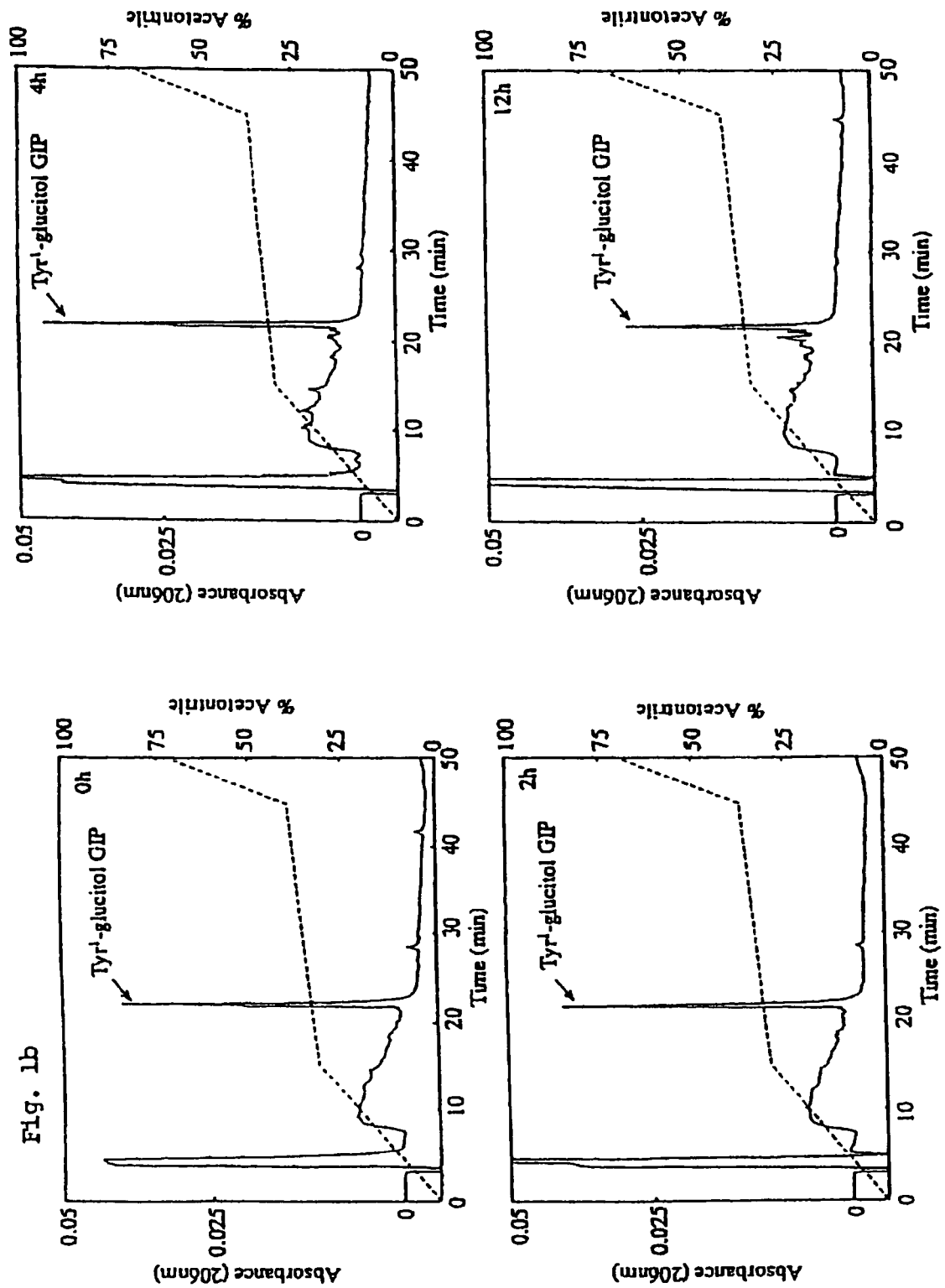
FIG. 1b illustrates degradation of GIP and $Tyr^1$ glucitol GIP by DPP IV.

Degradation of GIP and Tyr$^1$-glucitol GIP by DPP IV. FIG. 1 illustrates the typical peak profiles obtained from the HPLC separation of the products obtained from the incubation of GIP (FIG. 1a) or Tyr$^1$-glucitol GIP (FIG. 1b) with DPP IV for 0, 2, 4 and 12 hours. The retention times of GIP and Tyr$^1$-glucitol GIP at t=0 were 21.93 minutes and 21.75 minutes respectively. Degradation of GIP was evident after 4 hours incubation (54% intact), and by 12 hours the majority (60% of intact GIP was converted to the single product with a retention time of 21.61 minutes. Tyr$^1$-glucitol GIP remained almost completely intact throughout 2-12 hours incubation. Separation was on a Vydac C-18 colum using linear gradients of 0% to 31.5% acetonitrile over 15 minutes, to 38.5% over 30 minutes and from 38.5 to 70% acetonitrile over 5 minutes.

Figure 2A:
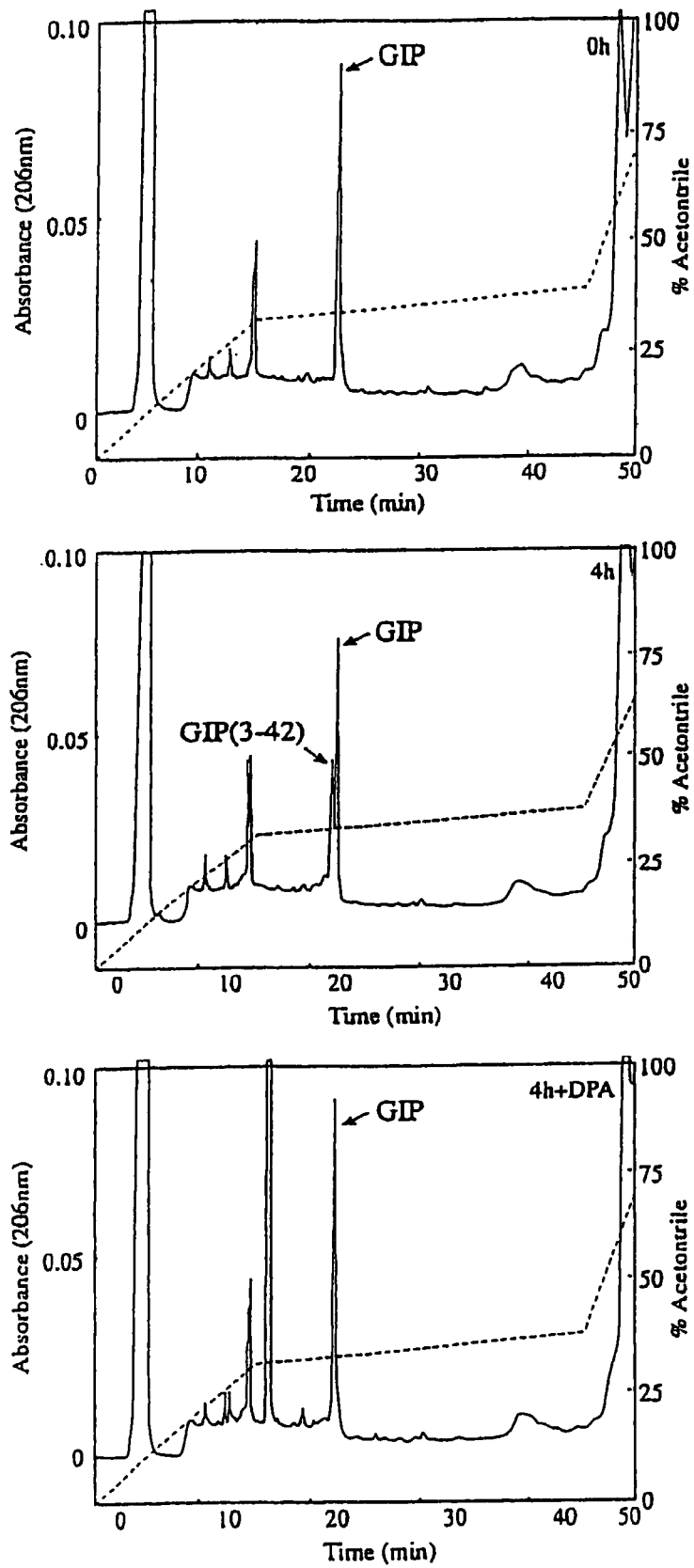
FIG. 2a illustrates degradation of GIP human plasma.
Figure 2B:
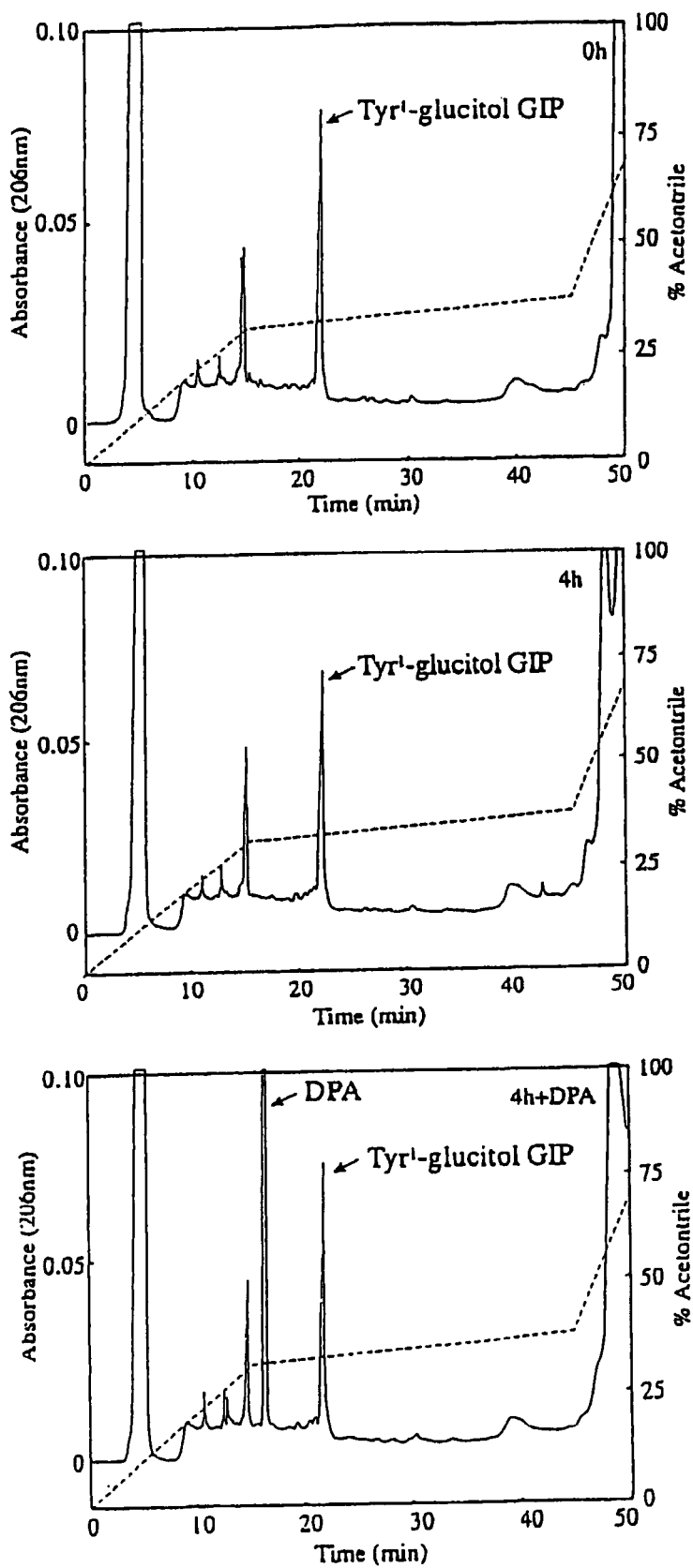
FIG. 2b illustrates degradation of GIP and $Tyr^1$-glucitol GIP by human plasma.

Degradation of GIP and Tyr$^1$-glucitol GIP by human plasma. FIG. 2 shows a set of typical HPLC profiles of the products obtained from the incubation of GIP or Tyr$^1$-glucitol GIP with human plasma for 0 and 4 h. GIP (FIG. 2a) with a retention time of 22.06 mm was readily metabolised by plasma within 4 hours incubation giving rise to the appearance of a major degradation peak with a retention time of 21.74 minutes. In contrast, the incubation of Tyr$^1$-glucitol GIP under similar conditions (FIG. 2b) did not result in the formation of any detectable degradation fragments during this time with only a single peak being observed with a retention time of 21.77 minutes. Addition of diprotin A, a specific inhibitor of DPP IV, to GIP during the 4 hours incubation completely inhibited degradation of the peptide by plasma. Peaks corresponding with intact GIP, GIP (3-42) and Tyr$^1$-glucitol GIP are indicated. A major peak corresponding to the specific DPP IV inhibitor tripeptide DPA appears in the bottom panels with retention time of 16.29 min.

Figure 3:
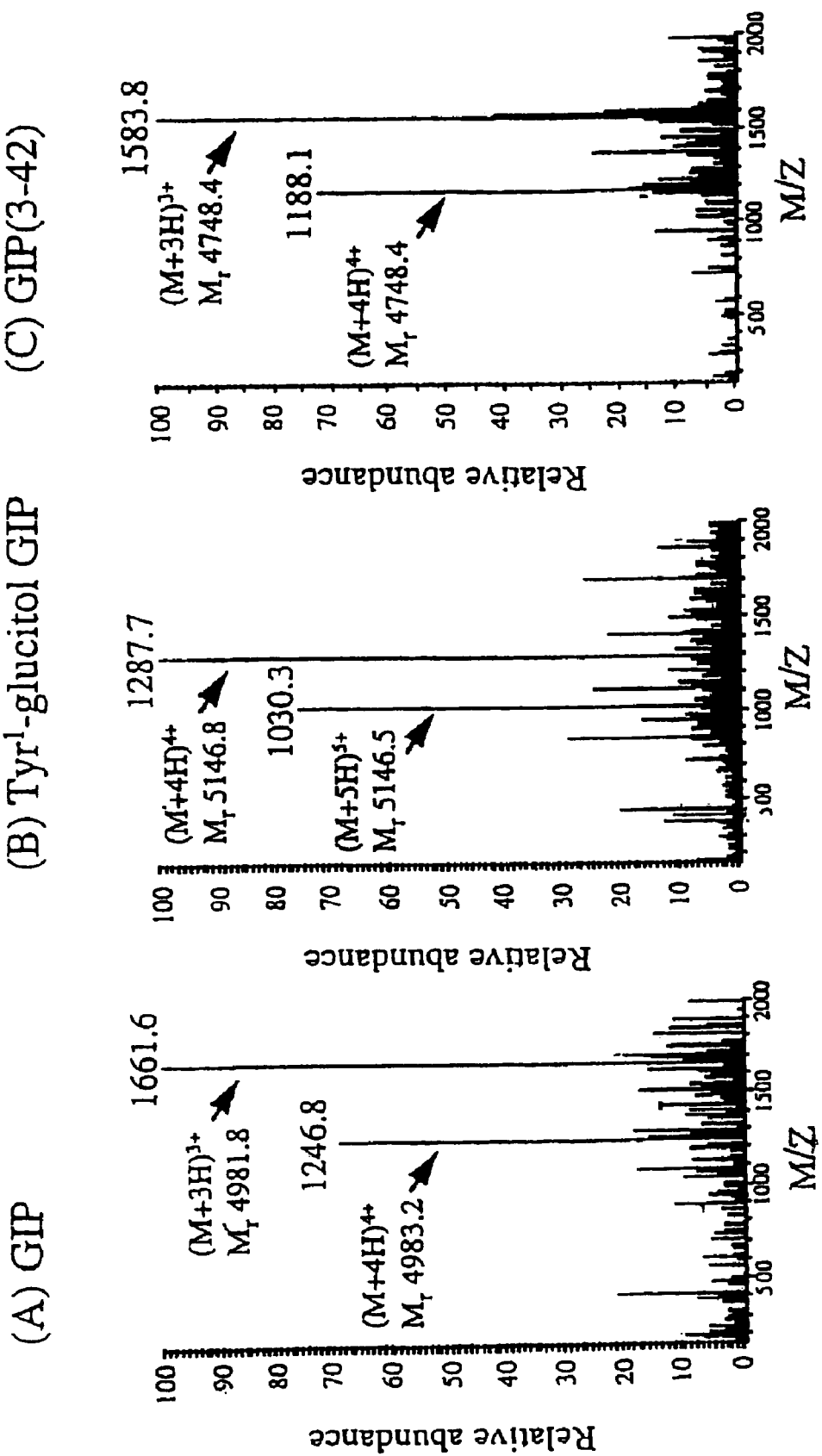
FIG. 3 illustrates electrospray ionization mass spectrometry of GIP, $Tyr^1$-glucitol GIP and the major degradation fragment GIP(3-42).

Identification of GIP degradation fragments by ESI-MS. FIG. 3 shows the monoisotopic molecular masses obtained for GIP, (panel A), Tyr$^1$-glucitol GIP (panel B) and the major plasma degradation fragment of GIP (panel C) using ESI-MS. The peptides analyzed were purified from plasma incubations as shown in FIG. 2. Peptides were dissolved (approximately 400 pmol) in 100 µl of water and applied to the LC/MS equipped with a microbore C-18 HPLC column. Samples (30 µl direct loop injection) were applied at a flow rate of 0.2 ml/min, under isocratic conditions 35% acetonitrile/water. Mass spectra were recorded using a quadripole ion trap mass analyzer. Spectra were collected using full ion scan mode over the mass-to-charge (m/z) range 150-2000. The molecular masses ($M_r$) of GIP and related structures were determined from ESI-MS profiles using prominent multiple charged ions and the following equation $M_r=iM_i-iM_h$. The exact molecular mass ($M_r$) of the peptides were calculated using the equation $M_r=iM_i-iM_h$ as defined in Research Design and Methods. After spectral averaging was performed, prominent multiple charges species $(M+3H)^{3+}$ and $(M+4H)^{4+}$ were detected from GIP at m/z 1661.6 and 1246.8, corresponding to intact $M_r$ 4981.8 and 4983.2 Da, respectively (FIG. 3A). Similarly, for Tyr$^1$-glucitol GIP $((M+4H)^{4+}$ and $(M+5H)^{5+})$ were detected at m/z 1287.7 and 1030.3, corresponding to intact molecular masses of $M^r$ 5146.8 and 5146.5 Da, respectively (FIG. 3B). The difference between the observed molecular masses of the quadruply charged GIP and the N-terminally modified GIP species (163.6 Da) indicated that the latter peptide contained a single glucitol adduct corresponding to Tyr$^1$-glucitol GIP. FIG. 3C shows the prominent multiply charged species $(M+3H)^{3+}$ and $(M+4H)^{4+}$ detected from the major fragment of GIP at m/z 1583.8 and 1188.1, corresponding to intact $M^r$ 4748.4 and 4748 Da, respectively (FIG. 3C). This corresponds with the theoretical mass of the N-terminally truncated form of the peptide GIP(3-42). This fragment was also the major degradation product of DPP IV incubations (data not shown).

Figure 4:
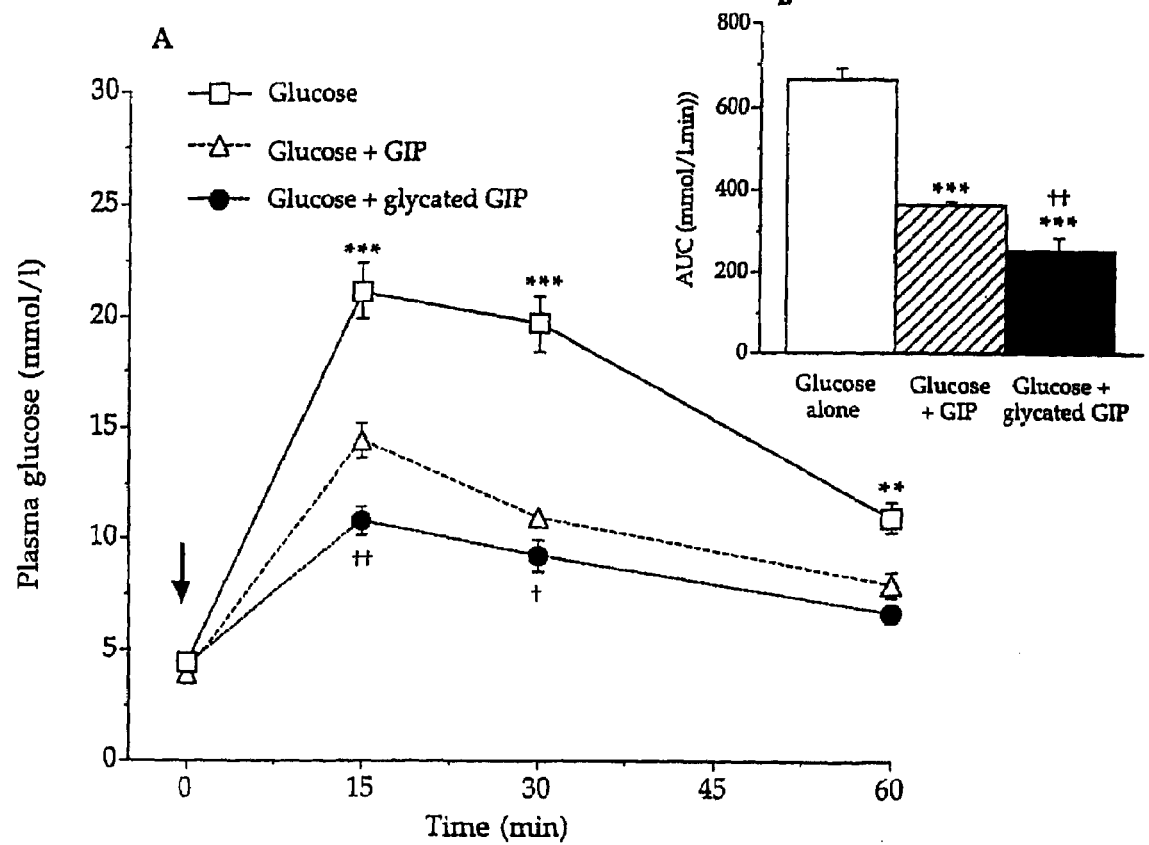
FIG. 4 shows the effects of GIP and glycated GIP on plasma glucose homeostasis.

Effects of GIP and Tyr$^1$-glucitol GIP on plasma glucose homeostasis. FIGS. 4 and 5 show the effects of intraperitoneal (ip) glucose alone (18 mmol.kg) (control group), and glucose in combination with GIP or Tyr$^1$-glucitol GIP (10 nmol/kg) on plasma glucose and insulin concentrations.

(4A) Plasma glucose concentrations after i.p. glucose alone (18 mmol/kg) (control group), or glucose in combination with either GIP of Tyr$^1$-glucitol GIP (10 nmol/kg). The time of injection is indicated by the arrow (0 min). (4B) Plasma glucose AUC calues for 0-60 min post injection. Values are mean±SEM for six rats. P<0.01, *P<0.001 compared with GIP and Tyr$^1$-glucitol GIP; tP<0.05, ttP<0.01 compared with non-glucated GIP.

(5A). Plasma insulin concentrates after i.p. glucose along (18 mmol/kg) (control group), or glucose in combination with either with GIP or glycated GIP (10 nmol/kg). The time of injection is indicated by the arrow. (5B) Plasma insulin AUC values were calculated for each of the 3 groups up to 90 minutes post injection. The time of injection is indicated by the arrow (0 min). Plasma insulin AUC values for 0-60 min post injection. Values are mean±SEM for six rats. *P<0.05, **P<0.001 compared with GIP and Tyr$^1$-glucitol GIP; tP<0.05, ttP<0.01 compared with non-glycated GIP.

Compared with the control group, plasma glucose concentrations and area under the curve (AUC) were significantly lower following administration of either GIP or Tyr$^1$-glucitol GIP (FIG. 4A, B). Furthermore, individual values at 15 and 30 minutes together with AUC were significantly lower following administration of Tyr$^1$-glucitol GIP as compared to GIP. Consistent with the established insulin-releasing properties of GIP, plasma insulin concentrations of both peptide-treated groups were significantly raised at 15 and 30 minutes compared with the values after administration of glucose alone (FIG. 5A). The overall insulin responses, estimated as AUC were also significantly greater for the two peptide-treated groups (FIG. 5B). Despite lower prevailing glucose concentrations than the GIP-treated group, plasma insulin response, calculated as AUC, following Tyr$^1$-glucitol GIP was significantly greater than after GIP (FIG. 5B). The significant elevation of plasma insulin at 30 minutes is of particular note, suggesting that the insulin-releasing action of Tyr$^1$-glucitol GIP is more protracted than GIP even in the face of a diminished glycemic stimulus (FIGS. 4A, 5A).

Discussion

The forty two amino acid GIP is an important incretin hormone released into the circulation from endocrine K-cells of the duodenum and jejunum following ingestion of food. The high degree of structural conservation of GIP among species supports the view that this peptide plays and important role in metabolism. Secretion of GIP is stimulated directly by actively transported nutrients in the gut lumen without a notable input from automatic nerves. The most important stimulants of GIP release are simple sugars and unsaturated long chain fatty acids, with amino acids exerting weaker effects. As with tGLP-1, the insulin-releasing effect of GIP is strictly glucose-dependent. This affords protection against hypoglycemia and thereby fulfills one of the most desirable features of any current or potentially new antidiabetic drug.

The present results demonstrate for the first time that Tyr$^1$-glucitol GIP displays profound resistance to serum and DPP IV degradation. Using ESI-MS the present study showed that native GIP was rapidly cleaved in vitro to a major 4748.4 Da degradation product, corresponding to GIP(3-42) which confirmed previous findings using matrix-assisted laser desorption ionization time-of-flight mass spectrometry. Serum degradation was completely inhibited by diprotin A (Ile-Pro-Ile), a specific competitive inhibitor of DPP IV, confirming this as the main enzyme for GIP inactivation in vivo.

In contrast, Tyr$^1$-glucitol GIP remained almost completely intact after incubation with serum or DPP IV for up to 12 hours. This indicates that glycation of GIP at the amino-terminal Tyr$^1$ residue masks the potential cleavage site from DPP IV and prevents removal of the Tyr-Ala$^2$ dipeptide from the N-terminus preventing the formation of GIP(3-42).

Consistent with in vitro protection against DPP IV, administration of Tyr$^1$-glucitol GIP significantly enhanced the antihyperglycemic activity and insulin-releasing action of the peptide when administered with glucose to rats. Native GIP enhanced insulin release and reduced the glycemic excursion as observed in many previous studies. However, amino-terminal glycation of GIP increased the insulin-releasing and antihyperglycemic actions of the peptide by 62% and 38% respectively, as estimated from AUC measurements. Detailed kinetic analysis is difficult due to necessary limitation of sampling times, but the greater insulin concentrations following Tyr$^1$-glucitol GIP as opposed to GIP at 30 minutes post-injection is indicative of a longer half-life. The glycemic rise was modest in both peptide-treated groups and glucose concentrations following injection of Tyr$^1$-glucitol GIP were consistently lower than after GIP. Since the insulinotropic actions of GIP are glucose-dependent, it is likely that the relative insulin-releasing potency of Tyr$^1$-glucitol GIP is greatly underestimated in the present in vivo experiments.

In vitro studies in the laboratory of the present inventors using glucose-responsive clonal B-cells showed that the insulin-releasing potency of Tyr$^1$-glucitol GIP was several order of magnitude greater than GIP and that its effectiveness was more sensitive to change of glucose concentrations within the physiological range. Together with the present in vivo observations, this suggests that N-terminal glycation of GIP confers resistance to DPP IV degradation whilst enhancing receptor binding and insulin secretory effects on the B-cell. These attributes of Tyr$^1$-glucitol GIP are fully expressed in vivo where DPP IV resistance impedes degradation of the peptide to GIP(3-42), thereby prolonging the half-life and ehancing effective concentrations of the intact biologically active peptide. It is thus possible that glycated GIP is enhancing insulin secretion in vivo both by enhanced potency at the receptor as well as improving DPP IV resistance. Thus numerous studies have shown that GIP (3-42) and other N-terminally modified fragments, including GIP(4-42), and GIP (17-42) are either weakly effective or inactive in stimulating insulin release. Furthermore, evidence exists that N-terminal deletions of GIP result in receptor antagonist properties in GIP receptor transfected Chinese hamster kidney cells [9], suggesting that inhibition of GIP catabolism would also reduce the possible feedback antagonism at the receptor level by the truncated GIP(3-42).

In addition to its insulinotopic actions, a number of other potentially important extrapancreatic actions of GIP may contribute to the enhanced antihyperglycemic activity and other beneficial metabolic effects of Tyr$^1$-glucitol GIP. These include the stimulation of glucose uptake in adipocytes, increased synthesis of fatty acids and activation of lipoprotein lipase in adipose tissue. GIP also promotes plasma triglyceride clearance in response to oral fat loading. In liver, GIP has been shown to enhance insulin-dependent inhibition of glycogenolysis. GIP also reduces both glucagon-stimulated lipolysis in adipose tissue as well as hepatic glucose production. Finally, recent findings indicate that GIP has a potent effect on glucose uptake and metabolism in mouse isolated diaphragm muscle. This latter action may be shared with tGLP-1 and both peptides have additional benfits of stimulating somatostatin secretion and slowing down gastric emptying and nutrient absorption.

In conclusion, this study has demonstrated for the first time that the glycation of GIP at the amino-terminal $Tyr^1$ residue limits GIP catabolism through impairment of the proteolytic actions of serum peptidases and thus prolongs its half-life in vivo. This effect is accompanied by enhanced antihyperglycemic activity and raised insulin concentrations in vivo, suggesting that such DPP IV resistant analogues should be explored alongside tGLP-1 as potentially useful therapeutic agents for NIDDM. $Ty^1$-glucitol GIP appears to be particularly interesting in this regard since such amino-terminal modification of GIP enhances rather than impairs glucose-dependent insulinotropic potency as was observed recently for tGLP-1.

EXAMPLE 3

This example further looked at the ability of additional N-terminal structural modifications of GIP in preventing inactivation by DPP and in plasma and their associated increase in both the insulin-releasing potency and potential therapeutic value. Native human GIP, glycated GIP, acetylated GIP and a number of GIP analogues with N-terminal amino acid substitutions were tested.

Materials and Methods

Reagents

High-performance liquid chromatography (HPLC) grade acetonitrile was obtained from Rathburn (Walkersburn, Scotland). Sequencing grade trifluroacetic acid (TFA) was obtained from Aldrich (Poole, Dorset, UK). Dipeptidyl peptidase IV was purchased from Sigma (Poole, Dorset, UK), and Diprotin A was purchased from Calibiochem Novabiochem (Beeston, Nottingham, UK). RPMI 1640 tissue culture medium, fetal calf serum, penicillin and streptomycin were all purchased from Gibco (Paisley, Strathclyde UK). All water used in these experiments was purified using a Milli-Q, Water Purification System (Millipore, Milford, Mass., USA). All other chemicals used were of the highest purity available.

Synthesis of GIP and N-terminally modified GIP analogues

GIP, GIP(Abu2), GIP(Sar2), GIP(Ser2), GIP(Gly2) and GIP(Pro3) were sequentially synthesised on an Applied Biosystems automated peptide synthesizer (model 432A) using standard solid-phase Fmoc procedure, starting with an Fmoc-Gln-Wang resin. Following cleavage from the resin by trifluoroacetic acid:water, thioanisole, ethanedithiol (90/2.5/5/2.5, a total volume of 20 ml/g resin), the resin was removed by filtration and the filtrate volume was decreased under reduced pressure. Dry diethyl ether was slowly added until a precipitate was observed. The precipitate was collected by low-speed centrifugation, resuspended in diethyl ether and centrifuged again, this procedure being carried out at least five times. The pellets were then dried in vacuo and judged pure by reversed-phase HPLC on a Waters Millennium 2010 chromatography system (Software version 2.1.5.). N-terminal glycated and acetylated GIP were prepared by minor modification of a published method.

Electrospray ionization-mass spectrometry (ESI-MS) was carred out as described in Example 2.

Degradation of GIP and novel GIP analogues by DPP IV and human plasma was carried out as described in Example 2.

Culture of Insulin Secreting Cells

BRIN-BD11 cells [30] were cultured in sterile tissue culture flasks (Corning, Glass Works, UK) using RPMI-1640 tissue culture medium containing 10% (v/v) foetal calf serum, 1% (v/v) antibiotics (100 U/ml penicillin, 0.1 mg/ml streptomycin) and 11.1 mM glucose. The cells were maintained at 37° C. in an atmosphere of 5% $CO_2$ and 95% air using a LEEC incubator (Laboratory Technical Engineering, Nottingham, UK).

Acute Tests for Insulin Secretion

Before experimentation, the cells were harvested from the surface of the tissue culture flasks with the aid of trypsin/EDTA (Gibco, Paisley, Strathclyde, UK), seeded into 24-multiwell plates (Nunc, Roskilde, Denmark) at a density of $1.5 \times 10^5$ cells per well, and allowed to attach overnight at 37° C. Acute tests for insulin release were preceded by 40 mm pre-incubation at 37° C. in 1.0 ml Krebs Ringer bicarbonate buffer (115 mM NaCl, 4.7 mM KCl, 1.28 mM $CaCl_2$, 1.2 mM $KH_2PO_4$, 1.2 mM $MgSO_4$, 10 mM $NaHCO_3$, 5 g/l bovine serum albumin, pH 7.4) supplemented with 1.1 mM glucose. Test incubations were performed (n=12) at two glucose concentrations (5.6 mM and 16.7 mM) with a range of concentrations ($10^{-13}$ to $10^{-8}$ M) of GIP or GIP analogues. After 20 mm incubation, the buffer was removed from each well and aliquots (200 µl) were used for measurement of insulin by radioimmunoassay [31].

Statistical Analysis

Results are expressed as mean±S.E.M. and values were compared using the Student's unpaired t-test. Groups of data were considered to be significantly different if P<0.05.

Results and Discussion

Structural identification of GIP and GIP analogues by ESI-MS

The monoisotopic molecular masses of the peptides were determined using ESI-MS. After spectral averaging was performed, prominent multiple charged species $(M+3H)^{3+}$ and $(M+4H)^{4+}$ were detected for each peptide. Calculated molecular masses confirmed the structural identity of synthetic GIP and each of the N-terminal analogues.

Degradation of GIP and Novel GIP Analogues by DPP-IV

FIGS. 6-11 illustrate the typical peak profiles obtained from the HPLC separation of the reaction products obtained from the incubation of GIP, GIP(Abu2), GIP(Sar2), GIP (Ser2), glycated GIP and acetylated GIP with DPP IV, for 0, 2, 4, 8 and 24 h. The results summarised in Table 1 indicate that glycated GIP, acetylated GIP, GIP(Ser2) are GIP(Abu2) more resistant than native GIP to in vitro degradation with DPP IV. From these data GIP(Sar2) appears to be less resistant.

Degradation of GIP and GIP Analogues by Human Plasma

FIGS. 12-16 show a representative set of HPLC profiles obtained from the incubation of GIP and GIP analogues with human plasma for 0, 2, 4, 8 and 24 h. Observations were also made after incubation for 24 h in the presence of DPA. These results are summarised in Table 2 are broadly comparable with DPP IV incubations, but conditions which more closely mirror in vivo conditions are less enzymatically severe. GIP was rapidly degraded by plasma. In comparison, all analogues tested exhibited resistance to plasma degradation, including GIP(Sar2) which from DPP IV data appeared least resistant of the peptides tested. DPA substantially inhibited degradation of GIP and all analogues tested with complete abolition of degradation in the cases of GIP(Abu2), GIP(Ser2) and glycated GIP. This indicates that DPP IV is a key factor in the in vivo degradation of GIP.

Dose-Dependent Effects of GIP and Novel GIP Analogues on Insulin Secretion

FIGS. 17-30 show the effects of a range of concentrations of GIP, GIP(Abu2), GIP(Sar2), GIP(Ser2), acetylated GIP, glycated GIP, GIP(Gly2) and GIP(Pro3) on insulin secretion from BRIN-BD11 cells at 5.6 and 16.7 mM glucose. Native GIP provoked a prominent and dose-related stimulation of insulin secretion. Consistent with previous studies [28], the glycated GIP analogue exhibited a considerably greater insulinotropic response compared with native peptide. N-terminal acetylated GIP exhibited a similar pattern and the GIP(Ser2) analogue also evoked a strong response. From these tests, GIP(Gly2) and GIP(Pro3) appeared to the least potent analogues in terms of insulin release. Other stable analogues tested, namely GIP(Abu2) and GIP(Sar2), exhibited a complex pattern of responsiveness dependent on glucose concentration and dose employed. Thus very low concentrations were extremely potent under hyperglycaemic conditions (16.7 mM glucose). This suggests that even these analogues may prove therapeutically useful in the treatment of type 2 diabetes where insulinotropic capacity combined with in vivo degradation dictates peptide potency.

TABLE 1

% Intact peptide remaining after incubation with DPPIV

| Peptide | % Intact peptide remaining after time (h) | | | | |
|---|---|---|---|---|---|
| | 0 | 2 | 4 | 8 | 24 |
| GIP 1-42 | 100 | 52 ± 1 | 23 ± 1 | 0 | 0 |
| Glycated GIP | 100 | 100 | 100 | 100 | 100 |
| GIP (Abu$^2$) | 100 | 38 ± 1 | 28 ± 2 | 0 | 0 |
| GIP (Ser$^2$) | 100 | 77 ± 2 | 60 ± 1 | 32 ± 4 | 0 |
| GIP (Sar$^2$) | 100 | 28 ± 2 | 8 | 0 | 0 |
| N-Acetyl-GIP | 100 | 100 | 100 | 100 | 0 |

TABLE 2

% Intact peptide remaining after incubation with human plasma

| Peptide | % Intact peptide remaining after incubations with human plasma | | | | | |
|---|---|---|---|---|---|---|
| | 0 | 2 | 4 | 8 | 24 | DPA |
| GIP 1-42 | 100 | 52 ± 1 | 23 ± 1 | 0 | 0 | 68 ± 2 |
| Glycated GIP | 100 | 100 | 100 | 100 | 100 | 100 |
| GIP (Abu$^2$) | 100 | 38 ± 1 | 28 ± 2 | 0 | 0 | 100 |
| GIP (Ser$^2$) | 100 | 77 ± 2 | 60 ± 1 | 32 ± 4 | 0 | 63 ± 3 |
| GIP (Sar$^2$) | 100 | 28 ± 2 | 8 | 0 | 0 | 100 |

Tables represent the percentage of intact peptide (i.e. GIP 1-42) relative to the major degradation product GIP 3-42. Values were taken from HPLC traces performed in triplicate and the mean and S.E.M. values calculated. DPA is diprotin A, a specific inhibitor of DPPIV.

The invention claimed is:

1. A pharmaceutical composition comprising a peptide analogue of GIP(1-42) and a pharmaceutically acceptable excipient, wherein the peptide analogue comprises at least 15 amino acid residues from the N-terminal end of GIP(1-42), wherein the amino acids at positions 4-15 of the peptide analogue are unsubstituted with respect to GIP(1-42), and wherein the peptide analogue comprises one or more amino acid substitutions or modifications selected from the group consisting of: an amino acid substitution or modification at position 1, an L-amino acid substitution or an amino acid modification at position 2, and an amino acid substitution or modification at position 3, with the proviso that the analogue is not tyrosine$^1$ glucitol GIP(1-42).

2. The pharmaceutical composition of claim 1, wherein the peptide analogue further comprises a modification by fatty acid addition at an epsilon amino group of at least one lysine residue.

3. The pharmaceutical composition of claim 2, wherein the lysine residue is chosen from the group consisting of Lys$^{16}$, Lys$^{30}$, Lys$^{32}$, Lys$^{33}$, and Lys$^{37}$.

4. A method for treating diabetes, comprising administering to an individual an effective amount of the pharmaceutical composition of claim 1.

5. The method of claim 4, wherein the diabetes is Type 2 diabetes.

6. The pharmaceutical composition of claim 1, wherein the peptide analogue is an analogue of human GIP.

7. A peptide analogue of GIP(1-42) comprising at least 15 amino acid residues from the N-terminal end of GIP(1-42), wherein the amino acids at positions 4-15 of the peptide analogue are unsubstituted with respect to GIP(1-42), and wherein the peptide analogue comprises:
   (a) N-terminal glycation and an amino acid substitution or modification at one or more of positions 1, 2, and 3;
   (b) amino acid substitution or modification at each of positions 1, 2, and 3;
   (c) amino acid substitution or modification at two of positions 1, 2, and 3, wherein each amino acid substitution or modification is selected from the group consisting of:
      (i) N-terminal glycation;
      (ii) N-terminal alkylation;
      (iii) N-terminal acetylation;
      (iv) N-terminal acylation;
      (v) the addition of an N-terminal isopropyl group;
      (vi) the addition of an N-terminal pyroglutamic acid;
      (vii) substitution at position 1 by a D-amino acid;
      (viii) substitution at position 1 by an L-amino acid;
      (ix) substitution at position 2 by a D-amino acid;
      (x) substitution at position 2 by an L-amino acid;
      (xi) substitution at position 2 by amino isobutyric acid or sarcosine;
      (xii) substitution at position 3 by a D-amino acid;
      (xiii) substitution at position 3 by an L-amino acid;
      (xiv) substitution at position 3 by amino isobutyric acid or sarcosine;
      (xv) conversion of the Ala$^2$-Glu$^3$ bond to a $\psi$[CH$_2$NH] bond;
      (xvi) conversion of the Ala$^2$-Glu$^3$ bond to a stable isostere bond; and
      (xvii) substitution by beta-alanine, an omega-amino acid, 3-amino propionic acid, 4-amino butyric acid, ornithine, citrulline, homoarginine, t-butylalanine, t-butylglycine, N-methylisoleucine, phenylglycine, cyclohexylalanine, norleucine, cysteic acid and methionine sulfoxide; and
   (d) amino acid substitution or modification at one of positions 1, 2, and 3, with the proviso that the analogue is not tyrosine$^1$ glucitol GIP(1-42), wherein the amino acid substitution or modification is selected from the group consisting of:
      (i) N-terminal glycation;
      (ii) N-terminal alkylation;
      (iii) N-terminal acetylation;
      (iv) N-terminal acylation;
      (v) the addition of an N-terminal isopropyl group;
      (vi) the addition of an N-terminal pyroglutamic acid;
      (vii) substitution at position 1 by a D-amino acid;
      (viii) substitution at position 1 by an L-amino acid;
      (ix) substitution at position 2 by an L-amino acid;
      (x) substitution at position 2 by amino isobutyric acid or sarcosine;
      (xi) substitution at position 3 by a D-amino acid;
      (xii) substitution at position 3 by an L-amino acid;
      (xiii) substitution at position 3 by amino isobutyric acid or sarcosine;
      (xiv) conversion of the Ala$^2$-Glu$^3$ bond to a $\psi$[CH$_2$NH] bond;
      (xv) conversion of the Ala$^2$-Glu$^3$ bond to a stable isostere bond; and
      (xvi) substitution by beta-alanine, an omega-amino acid, 3-amino propionic acid, 4-amino butyric acid, ornithine, citrulline, homoarginine, t-butylalanine, t-butylglycine, N-methylisoleucine, phenylglycine, cyclohexylalanine, norleucine, cysteic acid and methionine sulfoxide.

8. The peptide analogue of claim 7, further comprising a modification by fatty acid addition at an epsilon amino group of at least one lysine residue.

9. The peptide analogue of claim 8, wherein the lysine residue is chosen from the group consisting of Lys$^6$, Lys$^{30}$, Lys$^{32}$, Lys$^{33}$, and Lys$^{37}$.

10. The peptide analogue of claim 7, wherein the peptide analogue is resistant to degradation by DPPIV relative to native GIP(1-42).

11. The peptide analogue of claim 7, wherein the peptide analogue enhances insulin secretion or delays glucose absorption.

12. A pharmaceutical composition comprising the peptide analogue of claim 7.

13. A method for treating diabetes, comprising administering to an individual an effective amount of the peptide analogue of claim 7.

14. The method of claim 13, wherein the diabetes is Type 2 diabetes.

15. The peptide analogue of claim 7, wherein the peptide analogue is an analogue of human GIP.

16. A peptide analogue of GIP(1-42) comprising at least 15 amino acid residues from the N-terminal end of GIP(1-42), wherein the amino acids at positions 4-15 of the peptide analogue are unsubstituted with respect to GIP(1-42), and wherein the peptide analogue comprises:
(a) N-terminal glycation and an amino acid substitution or modification at one or more of positions 1, 2, and 3;
(b) amino acid substitution or modification at each of positions 1, 2, and 3;
(c) amino acid substitution or modification at two of positions 1, 2, and 3, wherein each amino acid substitution or modification is selected from the group consisting of:
  (i) N-terminal glycation;
  (ii) N-terminal alkylation;
  (iii) N-terminal acetylation;
  (iv) N-terminal acylation;
  (v) the addition of an N-terminal isopropyl group;
  (vi) the addition of an N-terminal pyroglutamic acid;
  (vii) substitution at position 1 by a D-amino acid;
  (viii) substitution at position 1 by an L-amino acid;
  (ix) substitution at position 2 by a D-amino acid;
  (x) substitution at position 2 by an L-amino acid;
  (xi) substitution at position 2 by amino isobutyric acid or sarcosine;
  (xii) substitution at position 3 by a D-amino acid;
  (xiii) substitution at position 3 by an L-amino acid;
  (xiv) substitution at position 3 by amino isobutyric acid or sarcosine;
  (xv) conversion of the $Ala^2$-$Glu^3$ bond to a $\psi[CH_2NH]$ bond;
  (xvi) conversion of the $Ala^2$-$Glu^3$ bond to a stable isostere bond; and
  (xvii) substitution by beta-alanine, an omega-amino acid, 3-amino propionic acid, 4-amino butyric acid, ornithine, citrulline, homoarginine, t-butylalanine, t-butylglycine, N-methylisoleucine, phenylglycine, cyclohexylalanine, norleucine, cysteic acid and methionine sulfoxide; or
(d) amino acid substitution or modification at one of positions 1, 2, and 3, with the proviso that the analogue is not $tyrosine^1$ glucitol GIP(1-42), wherein the amino acid substitution or modification is selected from the group consisting of:
  (i) N-terminal glycation;
  (ii) N-terminal alkylation;
  (iii) N-terminal acetylation;
  (iv) N-terminal acylation;
  (v) the addition of an N-terminal isopropyl group;
  (vi) the addition of an N-terminal pyroglutamic acid;
  (vii) substitution at position 1 by an L-amino acid;
  (viii) substitution at position 2 by an L-amino acid;
  (ix) substitution at position 2 by amino isobutyric acid or sarcosine;
  (ix) substitution at position 3 by an L-amino acid;
  (xi) substitution at position 3 by amino isobutyric acid or sarcosine;
  (xii) conversion of the $Ala^2$-$Glu^3$ bond to a $\psi[CH_2NH]$ bond;
  (xiii) conversion of the $Ala^2$-$Glu^3$ bond to a stable isostere bond; and
  (xiv) substitution by beta-alanine, an omega-amino acid, 3-amino propionic acid, 4-amino butyric acid, ornithine, citrulline, homoarginine, t-butylalanine, t-butylglycine, N-methylisoleucine, phenylglycine, cyclohexylalanine, norleucine, cysteic acid and methionine sulfoxide.

17. The peptide analogue of claim 16, further comprising a modification by fatty acid addition at an epsilon amino group of at least one lysine residue.

18. The peptide analogue of claim 17, wherein the lysine residue is chosen from the group consisting of $Lys^{16}$, $Lys^{30}$, $Lys^{32}$, $Lys^{33}$, and $Lys^{37}$.

19. The peptide analogue of claim 16, wherein the peptide analogue is resistant to degradation by DPPIV relative to native GIP(1-42).

20. The peptide analogue of claim 16, wherein the peptide analogue enhances insulin secretion or delays glucose absorption.

21. A pharmaceutical composition comprising the peptide analogue of claim 16.

22. A method for treating diabetes, comprising administering to an individual an effective amount of the peptide analogue of claim 16.

23. The method of claim 22, wherein the diabetes is Type 2 diabetes.

24. The peptide analogue of claim 16, wherein the peptide analogue is an analogue of human GIP.

25. A peptide analogue of GIP(1-42) comprising at least 15 amino acid residues from the N-terminal end of GIP(1-42), the analogue comprising N-terminal glycation and an amino acid substitution or modification at one or more of positions 1, 2 and 3.

26. The peptide analogue of claim 25, further comprising one or more of the following amino acid substitutions: substitution at position 2 by proline, lysine, serine, glycine, a D-amino acid, 4-amino butyric acid (Abu), amino isobutyric acid (Aib), or sarcosine, or substitution at position 3 by proline, lysine, serine, a D-amino acid, or sarcosine.

27. The peptide analogue of claim 25, further comprising a modification by fatty acid addition at an epsilon amino group of at least one lysine residue.

28. The peptide analogue of claim 27, wherein the lysine residue is chosen from the group consisting of $Lys^{16}$, $Lys^{30}$, $Lys^{32}$, $Lys^{33}$, and $Lys^{37}$.

29. A pharmaceutical composition comprising a peptide analogue of claim 25.

30. A method for treating diabetes, comprising administering to an individual an effective amount of the peptide analogue of claim 25.

31. The method of claim 30, wherein the diabetes is Type 2 diabetes.

32. The peptide analogue of claim 25, wherein the peptide analogue is an analogue of human GIP.

33. A peptide analogue of GIP(1-42) comprising at least 15 amino acid residues from the N-terminal end of GIP(1-42), the analogue comprising an N-alkylated amino acid at position 1.

34. The peptide analogue of claim 33, wherein the peptide analogue further comprises an amino acid substitution or modification at one or more of positions 1, 2 or 3.

35. The peptide analogue of claim 33, further comprising one or more of the following amino acid substitutions: substitution at position 2 by proline, lysine, serine, glycine, a D-amino acid, 4-amino butyric acid (Abu), amino isobutyric acid (Aib), or sarcosine, or substitution at position 3 by proline, lysine, serine, a D-amino acid, or sarcosine.

36. The peptide analogue of claim 33, further comprising a modification by fatty acid addition at an epsilon amino group of at least one lysine residue.

37. The peptide analogue of claim 36, wherein the lysine residue is chosen from the group consisting of $Lys^{16}$, $Lys^{30}$, $Lys^{32}$, $Lys^{33}$, and $Lys^{37}$.

38. A pharmaceutical composition comprising a peptide analogue of claim 33.

39. A method for treating diabetes, comprising administering to an individual an effective amount of the peptide analogue of claim 33.

40. The method of claim 39, wherein the diabetes is Type 2 diabetes.

41. The peptide analogue of claim 33, wherein the peptide analogue is an analogue of human GIP.

42. A peptide analogue of GIP(1-42) comprising at least 15 amino acid residues from the N-terminal end of GIP(1-42), the analogue comprising an N-acetylated amino acid at position 1.

43. The peptide analogue of claim 42, wherein the peptide analogue further comprises an amino acid substitution or modification at one or more of positions 1, 2 or 3.

44. The peptide analogue of claim 42, further comprising one or more of the following amino acid substitutions: substitution at position 2 by proline, lysine, serine, glycine, a D-amino acid, 4-amino butyric acid (Abu), amino isobutyric acid (Aib), or sarcosine, or substitution at position 3 by proline, lysine, serine, a D-amino acid, or sarcosine.

45. The peptide analogue of claim 42, further comprising a modification by fatty acid addition at an epsilon amino group of at least one lysine residue.

46. The peptide analogue of claim 45, wherein the lysine residue is chosen from the group consisting of $Lys^{16}$, $Lys^{30}$, $Lys^{32}$, $Lys^{33}$, and $Lys^{37}$.

47. A pharmaceutical composition comprising a peptide analogue of claim 42.

48. A method for treating diabetes, comprising administering to an individual an effective amount of the peptide analogue of claim 42.

49. The method of claim 48, wherein the diabetes is Type 2 diabetes.

50. The peptide analogue of claim 42, wherein the peptide analogue is an analogue of human GIP.

51. A peptide analogue of GIP(1-42) comprising at least 15 amino acid residues from the N-terminal end of GIP(1-42), the analogue comprising an N-acylated amino acid at position 1.

52. The peptide analogue of claim 51, wherein the peptide analogue further comprises an amino acid substitution or modification at one or more of positions 1, 2 or 3.

53. The peptide analogue of claim 51, further comprising one or more of the following amino acid substitutions: substitution at position 2 by proline, lysine, serine, glycine, a D-amino acid, 4-amino butyric acid (Abu), amino isobutyric acid (Aib), or sarcosine, or substitution at position 3 by proline, lysine, serine, a D-amino acid, or sarcosine.

54. The peptide analogue of claim 51, further comprising a modification by fatty acid addition at an epsilon amino group of at least one lysine residue.

55. The peptide analogue of claim 54, wherein the lysine residue is chosen from the group consisting of $Lys^{16}$, $Lys^{30}$, $Lys^{32}$, $Lys^{33}$, and $Lys^{37}$.

56. A pharmaceutical composition comprising a peptide analogue of claim 51.

57. A method for treating diabetes, comprising administering to an individual an effective amount of the peptide analogue of claim 51.

58. The method of claim 57, wherein the diabetes is Type 2 diabetes.

59. The peptide analogue of claim 51, wherein the peptide analogue is an analogue of human GIP.

60. A peptide analogue of GIP(1-42) comprising at least 15 amino acid residues from the N-terminal end of GIP(1-42), the analogue comprising the addition of an N-terminal isopropyl group.

61. The peptide analogue of claim 60, wherein the peptide analogue further comprises an amino acid substitution or modification at one or more of positions 1, 2 or 3.

62. The peptide analogue of claim 60, further comprising one or more of the following amino acid substitutions: substitution at position 2 by proline, lysine, serine, glycine, a D-amino acid, 4-amino butyric acid (Abu), amino isobutyric acid (Aib), or sarcosine, or substitution at position 3 by proline, lysine, serine, a D-amino acid, or sarcosine.

63. The peptide analogue of claim 60, further comprising a modification by fatty acid addition at an epsilon amino group of at least one lysine residue.

64. The peptide analogue of claim 63, wherein the lysine residue is chosen from the group consisting of $Lys^{16}$, $Lys^{30}$, $Lys^{32}$, $Lys^{33}$, and $Lys^{37}$.

65. A pharmaceutical composition comprising a peptide analogue of claim 60.

66. A method for treating diabetes, comprising administering to an individual an effective amount of the peptide analogue of claim 60.

67. The method of claim 66, wherein the diabetes is Type 2 diabetes.

68. The peptide analogue of claim 60, wherein the peptide analogue is an analogue of human GIP.

69. A peptide analogue of GIP(1-42) comprising at least 15 amino acid residues from the N-terminal end of GIP(1-42), the analogue comprising the addition of an N-terminal pyroglutamic acid.

70. The peptide analogue of claim 69, wherein the peptide analogue further comprises an additional amino acid substitution or modification at one or more of positions 1, 2 or 3.

71. The peptide analogue of claim 69, further comprising one or more of the following amino acid substitutions: substitution at position 2 by proline, lysine, serine, glycine, a D-amino acid, 4-amino butyric acid (Abu), amino isobutyric acid (Aib), or sarcosine, or substitution at position 3 by proline, lysine, serine, a D-amino acid, or sarcosine.

72. The peptide analogue of claim 69, further comprising a modification by fatty acid addition at an epsilon amino group of at least one lysine residue.

73. The peptide analogue of claim 72, wherein the lysine residue is chosen from the group consisting of $Lys^{16}$, $Lys^{30}$, $Lys^{32}$, $Lys^{33}$, and $Lys^{37}$.

74. A pharmaceutical composition comprising a peptide analogue of claim 69.

75. A method for treating diabetes, comprising administering to an individual an effective amount of the peptide analogue of claim 69.

76. The method of claim 75, wherein the diabetes is Type 2 diabetes.

77. The peptide analogue of claim 69, wherein the peptide analogue is an analogue of human GIP.

78. A peptide analogue of GIP(1-42) comprising at least 15 amino acid residues from the N-terminal end of GIP(1-42), the analogue comprising amino acid substitution or modification at each of positions 1, 2 and 3.

79. The peptide analogue of claim 78, further comprising one or more of the following amino acid substitutions: substitution at position 2 by proline, lysine, serine, glycine, a D-amino acid, 4-amino butyric acid (Abu), amino isobutyric acid (Aib), or sarcosine, or substitution at position 3 by proline, lysine, serine, a D-amino acid, or sarcosine.

80. The peptide analogue of claim 78, further comprising a modification by fatty acid addition at an epsilon amino group of at least one lysine residue.

81. The peptide analogue of claim 80, wherein the lysine residue is chosen from the group consisting of $Lys^{16}$, $Lys^{30}$, $Lys^{32}$, $Lys^{33}$, and $Lys^{37}$.

82. A pharmaceutical composition comprising a peptide analogue of claim 78.

83. A method for treating diabetes, comprising administering to an individual an effective amount of the peptide analogue of claim 78.

84. The method of claim 83, wherein the diabetes is type 2 diabetes.

85. The peptide analogue of claim 78, wherein the peptide analogue is an analogue of human GIP.

86. A peptide analogue of GIP(1-42) comprising at least 15 amino acid residues from the N-terminal end of GIP(1-42), the analogue comprising amino acid substitution or modification at two of positions 1, 2 and 3, wherein each amino acid substitution or modification is selected from the group consisting of:
   (a) substitution at position 1 by a D-amino acid;
   (b) substitution at position 1 by an L-amino acid;
   (c) substitution at position 2 by a D-amino acid;
   (d) substitution at position 2 by an L-amino acid;
   (e) substitution at position 2 by amino isobutyric acid or sarcosine;
   (f) substitution at position 3 by a D-amino acid;
   (g) substitution at position 3 by an L-amino acid;
   (h) substitution at position 3 by amino isobutyric acid or sarcosine;
   (i) conversion of the $Ala^2$-$Glu^3$ bond to a $\psi[CH_2NH]$ bond;
   (j) conversion of the $Ala^2$-$Glu^3$ bond to a stable isostere bond; and
   (k) substitution by beta-alanine, an omega-amino acid, 3-amino propionic acid, 4-amino butyric acid, ornithine, citrulline, homoarginine, t-butylalanine, t-butylglycine, N-methylisoleucine, phenylglycine, cyclohexylalanine, norleucine, cysteic acid and methionine sulfoxide.

87. The peptide analogue of claim 86, wherein the amino acid substitutions are selected from the following: substitution at position 2 by proline, lysine, serine, glycine, a D-amino acid, 4-amino butyric acid (Abu), amino isobutyric acid (Aib), or sarcosine, or substitution at position 3 by proline, lysine, serine, a D-amino acid, or sarcosine.

88. The peptide analogue of claim 86, further comprising a modification by fatty acid addition at an epsilon amino group of at least one lysine residue.

89. The peptide analogue of claim 88, wherein the lysine residue is chosen from the group consisting of $Lys^{16}$, $Lys^{30}$, $Lys^{32}$, $Lys^{33}$, and $Lys^{37}$.

90. A pharmaceutical composition comprising a peptide analogue of claim 86.

91. A method for treating diabetes, comprising administering to an individual an effective amount of the peptide analogue of claim 86.

92. The method of claim 91, wherein the diabetes is Type 2 diabetes.

93. The peptide analogue of claim 86, wherein the peptide analogue is an analogue of human GIP.

94. A peptide analogue of GIP(1-42) comprising at least 15 amino acid residues from the N-terminal end of GIP(1-42), wherein the amino acids at positions 4-15 of the peptide analogue are unsubstituted with respect to GIP(1-42), and wherein the peptide analogue comprises at least one amino acid substitution or modification at one of positions 1, 2 or 3, with the proviso that the analogue is not $tyrosine^1$ glucitol GIP(1-42V) wherein the amino acid substitution or modification is selected from the group consisting of:
   (a) substitution at position 1 by a D-amino acid;
   (b) substitution at position 1 by an L-amino acid;
   (c) substitution at position 2 by an L-amino acid;
   (d) substitution at position 2 by amino isobutyric acid or sarcosine;
   (e) substitution at position 3 by a D-amino acid;
   (f) substitution at position 3 by an L-amino acid;
   (g) substitution at position 3 by amino isobutyric acid or sarcosine;
   (h) conversion of the $Ala^2$-$Glu^3$ bond to a $\psi[CH_2NH]$ bond;
   (i) conversion of the $Ala^2$-$Glu^3$ bond to a stable isostere bond; and
   (j) substitution by beta-alanine, an omega-amino acid, 3-amino propionic acid, 4-amino butyric acid, ornithine, citrulline, homoarginine, t-butylalanine, t-butylglycine, N-methylisoleucine, phenylglycine, cyclohexylalanine, norleucine, cysteic acid and methionine sulfoxide.

95. The peptide analogue of claim 94, wherein the amino acid substitutions are selected from the following: substitution at position 2 by proline, lysine, serine, glycine, 4-amino butyric acid (Abu), amino isobutyric acid (Aib), or sarcosine, or substitution at position 3 by proline, lysine, serine, a D-amino acid, or sarcosine.

96. The peptide analogue of claim 94, further comprising a modification by fatty acid addition at an epsilon amino group of at least one lysine residue.

97. The peptide analogue of claim 96, wherein the lysine residue is chosen from the group consisting of $Lys^{16}$, $Lys^{30}$, $Lys^{32}$, $Lys^{33}$, and $Lys^{37}$.

98. A pharmaceutical composition comprising a peptide analogue of claim 94.

99. A method for treating diabetes, comprising administering to an individual an effective amount of the peptide analogue of claim 94.

100. The method of claim 99 wherein the diabetes is Type 2 diabetes.

101. The peptide analogue of claim 94, wherein the peptide analogue is an analogue of human GIP.

102. A peptide analogue of GIP(1-42) comprising at least 15 amino acid residues from the N-terminal end of GIP(1-42), wherein the amino acids at positions 4-15 of the peptide analogue are unsubstituted with respect to GIP(1-42), and wherein the peptide analogue comprises at least one amino acid substitution or modification at one of positions 1, 2 or 3, with the proviso that the analogue is not tyrosine1 glucitol GIP(1-42), wherein the amino acid substitution or modification is selected from the group consisting of:
   (a) substitution at position 1 by an L-amino acid;
   (b) substitution at position 2 by an L-amino acid;
   (c) substitution at position 2 by amino isobutyric acid or sarcosine;
   (d) substitution at position 3 by an L-amino acid;
   (e) substitution at position 3 by amino isobutyric acid or sarcosine;
   (f) conversion of the $Ala^2$-$Glu^3$ bond to a $\psi[CH_2NH]$ bond;
   (g) conversion of the $Ala^2$-$Glu^3$ bond to a stable isostere bond; and (h) substitution by beta-alanine, an omega-amino acid, 3-amino propionic acid, 4-amino butyric acid, ornithine, citrulline, homoarginine, t-butylalanine, t-butylglycine, N-methylisoleucine, phenylglycine, cyclohexylalanine, norleucine, cysteic acid and methionine sulfoxide.

103. The peptide analogue of claim 102, wherein the amino acid substitutions are selected from the following: substitution at position 2 by proline, lysine, serine, glycine, 4-amino butyric acid (Abu), amino isobutyric acid (Aib), or sarcosine, or substitution at position 3 by proline, lysine, serine, or sarcosine.

104. The peptide analogue of claim 102, further comprising a modification by fatty acid addition at an epsilon amino group of at least one lysine residue.

105. The peptide analogue of claim 104, wherein the lysine residue is chosen from the group consisting of $Lys^{16}$, $Lys^{30}$, $Lys^{32}$, $Lys^{33}$, and $Lys^{37}$.

106. A pharmaceutical composition comprising a peptide analogue of claim 102.

107. A method for treating diabetes, comprising administering to an individual an effective amount of the peptide analogue of claim 102.

108. The method of claim 107, wherein the diabetes of Type 2 diabetes.

109. The peptide analogue of claim 102, wherein the peptide analogue is an analogue of human GIP.

110. A peptide analogue of GIP(1-42) comprising at least 15 amino acid residues from the N-terminal end of GIP(1-42), the analogue comprising a modification by fatty acid addition at an epsilon amino group of at least one lysine residue, and an amino acid substitution or modification at one or more of positions 1, 2 and 3.

111. The peptide analogue of claim 110, further comprising one or more of the following amino acid substitutions: substitution at position 2 by proline, lysine, serine, glycine, a D-amino acid, 4-amino butyric acid (Abu), amino isobutyric acid (Aib), or sarcosine, or substitution at position 3 by proline, lysine, serine, a D-amino acid, sarcosine, or N-terminal glycation.

112. The peptide analogue of claim 110, wherein the lysine residue is chosen from the group consisting of $Lys^{16}$, $Lys^{30}$, $Lys^{32}$, $Lys^{33}$, and $Lys^{37}$.

113. A pharmaceutical composition comprising a peptide analogue of claim 110.

114. A method for treating diabetes, comprising administering to an individual an effective amount of the peptide analogue of claim 110.

115. The method of claim 114, wherein the diabetes is Type 2 diabetes.

116. The peptide analogue of claim 110, wherein the peptide analogue is an analogue of human GIP.

117. A method for treating diabetes, comprising administering to an individual an effective amount of a pharmaceutical composition comprising a peptide analogue of GIP (1-42) comprising at least 15 amino acid residues from the N-terminal end of GIP(1-42), the analogue comprising an amino acid substitution or modification at one or more of positions 1, 2 or 3, with the proviso that the analogue is not $tyrosine^1$ glucitol GIP(1-42), and a pharmaceutically acceptable excipient.

118. The method of claim 117, further comprising a modification by fatty acid addition at an epsilon amino group of at least one lysine residue.

119. The method of claim 118, wherein the lysine residue is chosen from the group consisting of $Lys^{16}$, $Lys^{30}$, $Lys^{32}$, $Lys^{33}$, and $Lys^{37}$.

120. The method of claim 117, wherein the diabetes is Type 2 diabetes.

121. The method of claim 117, wherein the peptide analogue is an analogue of human GIP.

122. The method of claim 117, wherein the analogue comprises one or more of the following amino acid substitutions: substitution at position 2 by proline, lysine, serine, glycine, a D-amino acid, 4-amino butyric acid (Abu), amino isobutyric acid (Aib), or sarcosine, or substitution at position 3 by proline, lysine, serine, a D-amino acid, or sarcosine.

123. The method according to claim 122, wherein the substitution at position 2 is by a D-amino acid.

124. The method of claim 123, wherein the diabetes is Type 2 diabetes.

125. The method according to claim 123, wherein the substitution at position 2 is by D-alanine.

126. The method of claim 125, wherein the diabetes is Type 2 diabetes.

127. The method of claim 117, wherein the GIP analogue consists of 15 to 30 amino acids from the N-terminal end of GIP(1-42).

128. The method of claim 122, wherein the GIP analogue consists of 15 to 30 amino acids from the N-terminal end of GIP(1-42).

129. The method of claim 125, wherein the GIP analogue consists of 15 to 30 amino acids from the N-terminal end of GIP(1-42).

130. The method of claim 117, wherein the GIP analogue is a GIP(1-30) having said substitution.

131. The method of claim 122, wherein the GIP analogue is a GIP(1-30) having one or more said substitution(s).

132. The method of claim 125, wherein the GIP analogue is a GIP(1-30) having one or more said substitution(s).

133. The method of claim 117, wherein the GIP analogue comprises at least 30 amino acids from the N-terminal end of GIP(1-42).

134. The method of claim 122, wherein the GIP analogue comprises at least 30 amino acids from the N-terminal end of GIP(1-42).

135. The method of claim 125, wherein the GIP analogue comprises at least 30 amino acids from the N-terminal end of GIP(1-42).

* * * * *

UNITED STATES PATENT AND TRADEMARK OFFICE
CERTIFICATE OF CORRECTION

PATENT NO. : 7,326,688 B2  Page 1 of 1
APPLICATION NO. : 11/090825
DATED : February 5, 2008
INVENTOR(S) : O'Harte et al.

It is certified that error appears in the above-identified patent and that said Letters Patent is hereby corrected as shown below:

In claim 7, Col. 16, Line 11, delete "[ CH$_2$NH]" and replace it with --[CH$_2$NH]--.
In claim 9, Col. 16, Line 55, delete "Lys$^6$" and replace it with --Lys$^{16}$--.
In claim 16, Col. 17, Line 26, delete "(ix)" and replace it with --(x)--.
In claim 94, Col. 22, Line 5, delete "GIP(1-42V" and replace it with --GIP(1-42)--;
        at line 10, delete "1by" and replace it with --1 by--.
In claim 102, Col. 22, Line 54, delete "tyrosine1" and replace it with --tyrosine$^1$--.

Signed and Sealed this

Twelfth Day of August, 2008

JON W. DUDAS
*Director of the United States Patent and Trademark Office*